United States Patent
Slayton et al.

(10) Patent No.: US 8,764,687 B2
(45) Date of Patent: Jul. 1, 2014

(54) METHODS AND SYSTEMS FOR COUPLING AND FOCUSING ACOUSTIC ENERGY USING A COUPLER MEMBER

(75) Inventors: Michael H Slayton, Tempe, AZ (US); Peter G. Barthe, Phoenix, AZ (US); Paul M. Jaeger, Mesa, AZ (US)

(73) Assignee: Guided Therapy Systems, LLC, Mesa, AZ (US)

( * ) Notice: Subject to any disclaimer, the term of this patent is extended or adjusted under 35 U.S.C. 154(b) by 1048 days.

(21) Appl. No.: 12/116,828

(22) Filed: May 7, 2008

(65) Prior Publication Data

US 2008/0281237 A1    Nov. 13, 2008

Related U.S. Application Data

(60) Provisional application No. 60/916,502, filed on May 7, 2007.

(51) Int. Cl.
*A61N 7/00* (2006.01)

(52) U.S. Cl.
USPC ............. 601/2; 600/437; 600/459; 600/472

(58) Field of Classification Search
USPC ....... 424/9.5; 606/27; 600/437, 573; 366/127
See application file for complete search history.

(56) References Cited

U.S. PATENT DOCUMENTS

| | | |
|---|---|---|
| 2,427,348 A | 9/1947 | Bond et al. |
| 3,913,386 A | 10/1975 | Saglio |
| 3,965,455 A | 6/1976 | Hurwitz |
| 3,992,925 A | 11/1976 | Perilhou |
| 4,039,312 A | 8/1977 | Patru |
| 4,059,098 A | 11/1977 | Murdock |
| 4,101,795 A | 7/1978 | Fukumoto et al. |
| 4,213,344 A | 7/1980 | Rose |

(Continued)

FOREIGN PATENT DOCUMENTS

| | | |
|---|---|---|
| DE | 4029175 | 3/1992 |
| DE | 10140064 | 3/2003 |

(Continued)

OTHER PUBLICATIONS

Hassan et al, "Structure and Applications of Poly(vinyl alcohol) Hydrogels Produced by Conventional Crosslinking or by Freezing/Thawing Methods," Advances in Polymer Science, 2000, pp. 37-65, vol. 153.

(Continued)

*Primary Examiner* — Baisakhi Roy
(74) *Attorney, Agent, or Firm* — Michael J. Lang

(57) ABSTRACT

An exemplary system for coupling acoustic energy using an encapsulated coupler member comprises a display or indicator, a control system, a probe, and a coupler member. This invention provides a coupler member adjustably configured to perform at least one of (i) providing a standoff, (ii) focusing or defocusing energy, and (iii) coupling energy. An exemplary gel coupler member is configured to hold the shape of a lens geometry. In one aspect of the present invention, gel coupler member comprises water, glycerol, and polyvinyl alcohol, and exhibits an increased desiccation time and shelf life when compared to the prior art. The probe can comprise various probe and/or transducer configurations. In an exemplary embodiment, the probe delivers focused, unfocused, and/or defocused ultrasound energy to the region of interest. Imaging and/or monitoring may alternatively be coupled and/or co-housed with an ultrasound system contemplated by the present invention.

15 Claims, 17 Drawing Sheets

(56) References Cited

U.S. PATENT DOCUMENTS

| | | |
|---|---|---|
| 4,276,491 A | 6/1981 | Daniel |
| 4,315,514 A | 2/1982 | Drewes et al. |
| 4,325,381 A | 4/1982 | Glenn |
| 4,343,301 A | 8/1982 | Indech |
| 4,372,296 A | 2/1983 | Fahim |
| 4,381,007 A | 4/1983 | Doss |
| 4,381,787 A | 5/1983 | Hottinger |
| 4,397,314 A | 8/1983 | Vaguine |
| 4,409,839 A | 10/1983 | Tanezer |
| 4,441,486 A | 4/1984 | Pounds |
| 4,452,084 A | 6/1984 | Taenzer |
| 4,484,569 A | 11/1984 | Driller |
| 4,513,749 A | 4/1985 | Kino |
| 4,527,550 A | 7/1985 | Ruggera et al. |
| 4,528,979 A | 7/1985 | Marchenko et al. |
| 4,567,895 A | 2/1986 | Putzke |
| 4,586,512 A | 5/1986 | Do-Huu |
| 4,601,296 A | 7/1986 | Yerushalmi |
| 4,637,256 A | 1/1987 | Sugiyama et al. |
| 4,646,756 A | 3/1987 | Watmough |
| 4,663,358 A | 5/1987 | Hyon |
| 4,668,516 A | 5/1987 | Duraffourd et al. |
| 4,697,588 A | 10/1987 | Reichenberger |
| 4,757,820 A | 7/1988 | Itoh |
| 4,807,633 A | 2/1989 | Fry |
| 4,858,613 A | 8/1989 | Fry et al. |
| 4,860,732 A | 8/1989 | Hasegawa et al. |
| 4,865,041 A | 9/1989 | Hassler |
| 4,865,042 A | 9/1989 | Umemura |
| 4,867,169 A | 9/1989 | Machida et al. |
| 4,874,562 A | 10/1989 | Hyon |
| 4,875,487 A | 10/1989 | Seppi |
| 4,893,624 A | 1/1990 | Lele |
| 4,896,673 A | 1/1990 | Rose et al. |
| 4,917,096 A | 4/1990 | Englehart |
| 4,973,096 A | 4/1990 | Jaworski |
| 4,938,216 A | 7/1990 | Lele |
| 4,938,217 A | 7/1990 | Lele |
| 4,947,046 A | 8/1990 | Kawabata et al. |
| 4,951,653 A | 8/1990 | Fry et al. |
| 4,955,365 A | 9/1990 | Fry et al. |
| 4,958,626 A | 9/1990 | Nambu |
| 4,976,709 A | 12/1990 | Sand |
| 4,979,501 A | 12/1990 | Valchanov |
| 5,012,797 A | 5/1991 | Liang et al. |
| 5,036,855 A | 8/1991 | Fry et al. |
| 5,054,310 A | 10/1991 | Flynn |
| 5,054,470 A | 10/1991 | Fry et al. |
| 5,115,814 A | 5/1992 | Griffith |
| 5,117,832 A | 6/1992 | Sanghvi et al. |
| 5,123,418 A | 6/1992 | Saurel et al. |
| 5,143,063 A | 9/1992 | Fellner |
| 5,143,074 A | 9/1992 | Dory |
| 5,150,711 A | 9/1992 | Dory |
| 5,150,714 A | 9/1992 | Green |
| 5,156,144 A | 10/1992 | Iwasaki |
| 5,158,536 A | 10/1992 | Sekins |
| 5,163,421 A | 11/1992 | Bernstein et al. |
| 5,178,135 A | 1/1993 | Uchiyama et al. |
| 5,191,880 A | 3/1993 | McLeod |
| 5,209,720 A | 5/1993 | Unger |
| 5,224,467 A | 7/1993 | Oku |
| 5,230,334 A | 7/1993 | Klopotek |
| 5,230,338 A | 7/1993 | Allen et al. |
| 5,265,614 A * | 11/1993 | Hayakawa et al. ........... 600/459 |
| 5,267,985 A | 12/1993 | Shimada et al. |
| 5,269,297 A | 12/1993 | Weng |
| 5,282,797 A | 2/1994 | Chess |
| 5,295,484 A | 3/1994 | Marcus |
| 5,304,169 A | 4/1994 | Sand |
| 5,321,520 A | 6/1994 | Inga et al. |
| 5,360,268 A | 11/1994 | Hayashi |
| 5,370,121 A | 12/1994 | Reichenberger |
| 5,371,483 A | 12/1994 | Bhardwaj |
| 5,379,773 A | 1/1995 | Hornsby |
| 5,380,280 A | 1/1995 | Peterson |
| 5,383,917 A | 1/1995 | Desai et al. |
| 5,391,140 A | 2/1995 | Schaetzle |
| 5,391,197 A | 2/1995 | Burdette et al. |
| 5,406,503 A | 4/1995 | Williams, Jr. et al. |
| 5,419,327 A | 5/1995 | Rohwedder et al. |
| 5,435,311 A | 7/1995 | Umemura |
| 5,458,596 A | 10/1995 | Lax |
| 5,460,595 A | 10/1995 | Hall et al. |
| 5,471,988 A | 12/1995 | Fujio |
| 5,487,388 A | 1/1996 | Rello et al. |
| 5,492,126 A | 2/1996 | Hennige et al. |
| 5,496,256 A | 3/1996 | Bock |
| 5,501,655 A | 3/1996 | Rolt et al. |
| 5,503,320 A | 4/1996 | Webster et al. |
| 5,507,790 A | 4/1996 | Weiss |
| 5,520,188 A | 5/1996 | Hennige |
| 5,522,869 A | 6/1996 | Burdette |
| 5,523,058 A | 6/1996 | Umemura et al. |
| 5,524,620 A | 6/1996 | Rosenschein |
| 5,524,624 A | 6/1996 | Tepper |
| 5,524,625 A | 6/1996 | Okazaki et al. |
| 5,526,624 A | 6/1996 | Berg |
| 5,526,812 A | 6/1996 | Dumoulin et al. |
| 5,526,814 A | 6/1996 | Cline et al. |
| 5,526,815 A | 6/1996 | Granz |
| 5,540,235 A | 7/1996 | Wilson |
| 5,558,092 A | 9/1996 | Unger et al. |
| 5,560,362 A | 10/1996 | Sliwa et al. |
| 5,575,291 A | 11/1996 | Hayakawa |
| 5,575,807 A | 11/1996 | Faller |
| 5,577,502 A | 11/1996 | Darrow et al. |
| 5,577,991 A | 11/1996 | Akui et al. |
| 5,580,575 A | 12/1996 | Unger et al. |
| 5,601,526 A | 2/1997 | Chapelon et al. |
| 5,603,323 A | 2/1997 | Pflugrath et al. |
| 5,609,562 A | 3/1997 | Kaali |
| 5,615,091 A | 3/1997 | Palatnik |
| 5,617,858 A | 4/1997 | Taverna et al. |
| 5,618,275 A | 4/1997 | Bock |
| 5,620,479 A | 4/1997 | Diederich |
| 5,638,819 A | 6/1997 | Manwaring et al. |
| 5,647,373 A | 7/1997 | Paltieli |
| 5,655,538 A | 8/1997 | Lorraine |
| 5,657,760 A | 8/1997 | Ying |
| 5,658,328 A | 8/1997 | Johnson |
| 5,660,836 A | 8/1997 | Knowlton |
| 5,665,053 A | 9/1997 | Jacobs |
| 5,673,699 A | 10/1997 | Trahey et al. |
| 5,676,692 A | 10/1997 | Sanghvi et al. |
| 5,685,820 A | 11/1997 | Riek et al. |
| 5,690,608 A | 11/1997 | Watanabe et al. |
| 5,694,936 A | 12/1997 | Fujimoto |
| 5,697,897 A | 12/1997 | Buchholtz |
| 5,701,900 A | 12/1997 | Shehada et al. |
| 5,715,823 A | 2/1998 | Wood et al. |
| 5,720,287 A | 2/1998 | Chapelon et al. |
| 5,722,411 A | 3/1998 | Suzuki |
| 5,727,554 A | 3/1998 | Kalend et al. |
| 5,735,280 A | 4/1998 | Sherman et al. |
| 5,743,863 A | 4/1998 | Chapelon |
| 5,746,005 A | 5/1998 | Steinberg |
| 5,746,762 A | 5/1998 | Bass |
| 5,748,767 A | 5/1998 | Raab |
| 5,749,364 A | 5/1998 | Sliwa et al. |
| 5,755,228 A | 5/1998 | Wilson et al. |
| 5,755,753 A | 5/1998 | Knowlton |
| 5,762,066 A | 6/1998 | Seppi |
| 5,769,790 A | 6/1998 | Watkins |
| 5,795,297 A | 8/1998 | Daigle |
| 5,795,311 A | 8/1998 | Wess |
| 5,810,888 A | 9/1998 | Fenn |
| 5,817,013 A | 10/1998 | Ginn et al. |
| 5,817,021 A | 10/1998 | Reichenberger |
| 5,820,564 A | 10/1998 | Slayton |
| 5,823,962 A | 10/1998 | Schaetzle |
| 5,827,204 A | 10/1998 | Grandia et al. |
| 5,840,032 A | 11/1998 | Hatfield et al. |
| 5,844,140 A | 12/1998 | Seale |

(56) References Cited

U.S. PATENT DOCUMENTS

| | | |
|---|---|---|
| 5,853,367 A | 12/1998 | Chalek et al. |
| 5,869,751 A | 2/1999 | Bonin |
| 5,871,524 A | 2/1999 | Knowlton |
| 5,873,902 A | 2/1999 | Sanghvi et al. |
| 5,879,303 A | 3/1999 | Averkiou et al. |
| 5,882,557 A | 3/1999 | Hayakawa |
| 5,891,034 A | 4/1999 | Bucholz |
| 5,904,659 A | 5/1999 | Duarte et al. |
| 5,919,219 A | 7/1999 | Knowlton |
| 5,924,989 A | 7/1999 | Polz |
| 5,928,169 A | 7/1999 | Schatzle et al. |
| 5,931,805 A | 8/1999 | Brisken |
| 5,938,606 A | 8/1999 | Bonnefous |
| 5,938,612 A | 8/1999 | Kline-Schoder |
| 5,948,011 A | 9/1999 | Knowlton |
| 5,957,844 A | 9/1999 | Dekel |
| 5,957,882 A | 9/1999 | Nita et al. |
| 5,967,980 A | 10/1999 | Ferre et al. |
| 5,968,034 A | 10/1999 | Fullmer et al. |
| 5,971,949 A | 10/1999 | Levin et al. |
| 5,984,882 A | 11/1999 | Rosenschein et al. |
| 5,997,471 A | 12/1999 | Gumb et al. |
| 5,997,497 A | 12/1999 | Nita et al. |
| 6,004,262 A | 12/1999 | Putz et al. |
| 6,007,499 A | 12/1999 | Martin et al. |
| 6,022,327 A | 2/2000 | Chang |
| 6,036,646 A | 3/2000 | Barthe |
| 6,039,048 A | 3/2000 | Silberg |
| 6,042,556 A | 3/2000 | Beach et al. |
| 6,049,159 A | 4/2000 | Barthe |
| 6,050,943 A | 4/2000 | Slayton |
| 6,059,727 A | 5/2000 | Fowlkes |
| 6,071,239 A | 6/2000 | Cribbs et al. |
| 6,080,108 A | 6/2000 | Dunham |
| 6,086,535 A | 7/2000 | Ishibashi |
| 6,086,580 A | 7/2000 | Mordon et al. |
| 6,090,054 A | 7/2000 | Tagishi et al. |
| 6,093,883 A | 7/2000 | Sanghvi et al. |
| 6,101,407 A | 8/2000 | Groezinger |
| 6,106,469 A | 8/2000 | Suzuki et al. |
| 6,113,558 A | 9/2000 | Rosenschein et al. |
| 6,113,559 A | 9/2000 | Klopotek |
| 6,120,452 A | 9/2000 | Barthe |
| 6,135,971 A | 10/2000 | Hutchinson et al. |
| 6,139,499 A | 10/2000 | Wilk |
| 6,159,150 A | 12/2000 | Yale et al. |
| 6,171,244 B1 | 1/2001 | Finger et al. |
| 6,176,840 B1 | 1/2001 | Nishimura et al. |
| 6,183,426 B1 | 2/2001 | Akisada et al. |
| 6,183,502 B1 | 2/2001 | Takeuchi |
| 6,183,773 B1 | 2/2001 | Anderson |
| 6,190,323 B1 | 2/2001 | Digs |
| 6,190,336 B1 | 2/2001 | Duarte et al. |
| 6,193,658 B1 | 2/2001 | Wendelken et al. |
| 6,210,327 B1 | 4/2001 | Brackett et al. |
| 6,213,948 B1 | 4/2001 | Barthe |
| 6,216,029 B1 | 4/2001 | Paltieli |
| 6,233,476 B1 | 5/2001 | Strommer et al. |
| 6,234,990 B1 | 5/2001 | Rowe et al. |
| 6,241,753 B1 | 6/2001 | Knowlton |
| 6,246,898 B1 | 6/2001 | Vesely et al. |
| 6,251,074 B1 | 6/2001 | Averkiou et al. |
| 6,251,088 B1 | 6/2001 | Kaufman et al. |
| 6,268,405 B1 | 7/2001 | Yao |
| 6,273,864 B1 | 8/2001 | Duarte et al. |
| 6,280,402 B1 | 8/2001 | Ishibashi et al. |
| 6,287,257 B1 | 9/2001 | Matichuk |
| 6,296,619 B1 | 10/2001 | Brisken |
| 6,301,989 B1 | 10/2001 | Brown et al. |
| 6,311,090 B1 | 10/2001 | Knowlton |
| 6,315,741 B1 | 11/2001 | Martin |
| 6,322,509 B1 | 11/2001 | Pan et al. |
| 6,322,532 B1 | 11/2001 | D'Sa |
| 6,325,540 B1 | 12/2001 | Lounsberry et al. |
| 6,325,769 B1 | 12/2001 | Klopotek |
| 6,325,798 B1 | 12/2001 | Edwards et al. |
| 6,350,276 B1 | 2/2002 | Knowlton |
| 6,356,780 B1 | 3/2002 | Licato et al. |
| 6,361,531 B1 | 3/2002 | Hissong et al. |
| 6,375,672 B1 | 4/2002 | Aksan et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,390,982 B1 | 5/2002 | Bova et al. |
| 6,405,090 B1 | 6/2002 | Knowlton |
| 6,409,720 B1 | 6/2002 | Hissong |
| 6,413,253 B1 | 7/2002 | Koop et al. |
| 6,413,254 B1 | 7/2002 | Hissong et al. |
| 6,419,648 B1 | 7/2002 | Vitek et al. |
| 6,425,865 B1 | 7/2002 | Salcudean |
| 6,425,867 B1 | 7/2002 | Veazy |
| 6,425,912 B1 | 7/2002 | Knowlton |
| 6,428,477 B1 | 8/2002 | Mason |
| 6,428,532 B1 | 8/2002 | Doukas et al. |
| 6,430,446 B1 | 8/2002 | Knowlton |
| 6,432,067 B1 | 8/2002 | Martin |
| 6,432,101 B1 | 8/2002 | Weber et al. |
| 6,436,061 B1 | 8/2002 | Costantino |
| 6,438,424 B1 | 8/2002 | Knowlton |
| 6,440,071 B1 | 8/2002 | Slayton |
| 6,440,121 B1 | 8/2002 | Weber et al. |
| 6,443,914 B1 | 9/2002 | Costantino |
| 6,453,202 B1 | 9/2002 | Knowlton |
| 6,461,378 B1 | 10/2002 | Knowlton |
| 6,470,216 B1 | 10/2002 | Knowlton |
| 6,491,657 B2 | 12/2002 | Rowe |
| 6,500,121 B1 | 12/2002 | Slayton |
| 6,500,141 B1 | 12/2002 | Irion et al. |
| 6,508,774 B1 | 1/2003 | Acker |
| 6,511,428 B1 | 1/2003 | Azuma |
| 6,514,244 B2 | 2/2003 | Pope |
| 6,524,250 B1 | 2/2003 | Weber |
| 6,540,679 B2 | 4/2003 | Slayton |
| 6,540,685 B1 | 4/2003 | Rhoads et al. |
| 6,554,771 B1 | 4/2003 | Buil et al. |
| 6,569,099 B1 | 5/2003 | Babaev |
| 6,595,934 B1 | 7/2003 | Hissong et al. |
| 6,599,256 B1 | 7/2003 | Acker |
| 6,607,498 B2 | 8/2003 | Eshel |
| 6,623,430 B1 | 9/2003 | Slayton |
| 6,626,854 B2 | 9/2003 | Friedman et al. |
| 6,626,855 B1 | 9/2003 | Weng et al. |
| 6,638,226 B2 | 10/2003 | He et al. |
| 6,645,162 B2 | 11/2003 | Friedman |
| 6,662,054 B2 | 12/2003 | Kreindel |
| 6,663,627 B2 | 12/2003 | Francischelli |
| 6,665,806 B1 | 12/2003 | Shimizu |
| 6,666,835 B2 | 12/2003 | Martin et al. |
| 6,669,638 B1 | 12/2003 | Miller et al. |
| 6,685,640 B2 | 2/2004 | Fry et al. |
| 6,692,450 B1 | 2/2004 | Coleman |
| 6,699,237 B2 | 3/2004 | Weber et al. |
| 6,719,449 B1 | 4/2004 | Laugharn, Jr. et al. |
| 6,719,694 B2 | 4/2004 | Weng et al. |
| 6,749,624 B2 | 6/2004 | Knowlton |
| 6,775,404 B1 | 8/2004 | Pagoulatos et al. |
| 6,824,516 B2 | 11/2004 | Batten et al. |
| 6,835,940 B2 | 12/2004 | Morikawa et al. |
| 6,875,176 B2 | 4/2005 | Mourad |
| 6,882,884 B1 | 4/2005 | Mosk et al. |
| 6,887,239 B2 | 5/2005 | Elstrom |
| 6,889,089 B2 | 5/2005 | Behl et al. |
| 6,896,657 B2 | 5/2005 | Willis |
| 6,902,536 B2 | 6/2005 | Manna |
| 6,905,466 B2 | 6/2005 | Salgo et al. |
| 6,918,907 B2 | 7/2005 | Kelly |
| 6,920,883 B2 | 7/2005 | Bessette |
| 6,921,371 B2 | 7/2005 | Wilson |
| 6,932,771 B2 | 8/2005 | Whitmore |
| 6,936,044 B2 | 8/2005 | McDaniel |
| 6,936,046 B2 | 8/2005 | Hissong et al. |
| 6,948,843 B2 * | 9/2005 | Laugharn et al. .............. 366/127 |

(56) References Cited

U.S. PATENT DOCUMENTS

| | | |
|---|---|---|
| 6,953,941 B2 | 10/2005 | Nakano et al. |
| 6,958,043 B2 | 10/2005 | Hissong |
| 6,971,994 B1 | 12/2005 | Young et al. |
| 6,974,417 B2 | 12/2005 | Lockwood |
| 6,976,492 B2 | 12/2005 | Ingle |
| 6,992,305 B2 | 1/2006 | Maezawa et al. |
| 6,997,923 B2 | 2/2006 | Anderson |
| 7,006,874 B2 | 2/2006 | Knowlton et al. |
| 7,020,528 B2 | 3/2006 | Neev |
| 7,022,089 B2 | 4/2006 | Ooba et al. |
| 7,058,440 B2 | 6/2006 | Heuscher et al. |
| 7,063,666 B2 | 6/2006 | Weng et al. |
| 7,070,565 B2 | 7/2006 | Vaezy |
| 7,074,218 B2 | 7/2006 | Washington et al. |
| 7,094,252 B2 | 8/2006 | Koop |
| 7,115,123 B2 | 10/2006 | Knowlton et al. |
| 7,142,905 B2 | 11/2006 | Slayton |
| 7,179,238 B2 | 2/2007 | Hissong |
| 7,189,230 B2 | 3/2007 | Knowlton |
| 7,229,411 B2 | 6/2007 | Slayton |
| 7,235,592 B2 | 6/2007 | Muratoglu |
| 7,258,674 B2 | 8/2007 | Cribbs et al. |
| 7,273,459 B2 | 9/2007 | Desilets |
| 7,297,117 B2 | 11/2007 | Trucco et al. |
| 7,347,855 B2 | 3/2008 | Eshel |
| RE40,403 E | 6/2008 | Cho et al. |
| 7,393,325 B2 | 7/2008 | Barthe |
| 7,491,171 B2 | 2/2009 | Barthe et al. |
| 7,530,356 B2 | 5/2009 | Slayton |
| 7,530,958 B2 | 5/2009 | Slayton |
| 7,571,336 B2 | 8/2009 | Barthe |
| 7,601,120 B2 | 10/2009 | Moilanen et al. |
| 7,615,015 B2 | 11/2009 | Coleman |
| 7,615,016 B2 | 11/2009 | Barthe |
| 7,758,524 B2 | 7/2010 | Barthe |
| 7,824,348 B2 | 11/2010 | Barthe et al. |
| 7,955,281 B2 | 6/2011 | Pedersen et al. |
| 7,967,764 B2 | 6/2011 | Lidgren et al. |
| 8,057,389 B2 | 11/2011 | Barthe et al. |
| 8,128,618 B2 | 3/2012 | Gliklich et al. |
| 8,166,332 B2 | 4/2012 | Barthe et al. |
| 8,282,554 B2 | 10/2012 | Makin et al. |
| 2001/0009997 A1 | 7/2001 | Pope |
| 2001/0014780 A1 | 8/2001 | Martin et al. |
| 2001/0014819 A1 | 8/2001 | Ingle et al. |
| 2001/0031922 A1 | 10/2001 | Weng et al. |
| 2001/0039380 A1* | 11/2001 | Larson et al. .............. 600/437 |
| 2001/0041880 A1 | 11/2001 | Brisken |
| 2002/0000763 A1 | 1/2002 | Jones |
| 2002/0040199 A1 | 4/2002 | Klopotek |
| 2002/0040442 A1 | 4/2002 | Ishidera |
| 2002/0055702 A1 | 5/2002 | Atala |
| 2002/0062077 A1 | 5/2002 | Emmenegger et al. |
| 2002/0062142 A1 | 5/2002 | Knowlton |
| 2002/0082528 A1 | 6/2002 | Friedman et al. |
| 2002/0082589 A1 | 6/2002 | Friedman et al. |
| 2002/0095143 A1 | 7/2002 | Key |
| 2002/0128648 A1 | 9/2002 | Weber |
| 2002/0156400 A1 | 10/2002 | Babaev |
| 2002/0161357 A1 | 10/2002 | Anderson et al. |
| 2002/0165529 A1 | 11/2002 | Danek |
| 2002/0168049 A1 | 11/2002 | Schriever |
| 2002/0169394 A1* | 11/2002 | Eppstein et al. .............. 600/573 |
| 2002/0169442 A1 | 11/2002 | Neev |
| 2002/0173721 A1 | 11/2002 | Grunwald et al. |
| 2002/0193831 A1 | 12/2002 | Smith |
| 2003/0014039 A1 | 1/2003 | Barzell et al. |
| 2003/0018255 A1 | 1/2003 | Martin |
| 2003/0028113 A1 | 2/2003 | Gilbert et al. |
| 2003/0032900 A1 | 2/2003 | Ella |
| 2003/0036706 A1 | 2/2003 | Slayton |
| 2003/0040739 A1 | 2/2003 | Koop |
| 2003/0050678 A1 | 3/2003 | Sierra |
| 2003/0060736 A1 | 3/2003 | Martin et al. |
| 2003/0065313 A1 | 4/2003 | Koop et al. |
| 2003/0074023 A1 | 4/2003 | Kaplan |
| 2003/0083536 A1 | 5/2003 | Eshel |
| 2003/0097071 A1 | 5/2003 | Halmann |
| 2003/0125629 A1 | 7/2003 | Ustuner |
| 2003/0171678 A1 | 9/2003 | Batten et al. |
| 2003/0171701 A1 | 9/2003 | Babaev |
| 2003/0176790 A1 | 9/2003 | Slayton |
| 2003/0191396 A1 | 10/2003 | Sanghvi et al. |
| 2003/0200481 A1 | 10/2003 | Stanley |
| 2003/0212129 A1 | 11/2003 | Liu et al. |
| 2003/0212351 A1 | 11/2003 | Hissong et al. |
| 2003/0212393 A1 | 11/2003 | Knowlton et al. |
| 2003/0216795 A1 | 11/2003 | Harth |
| 2003/0220536 A1 | 11/2003 | Hissong |
| 2003/0220585 A1 | 11/2003 | Hissong |
| 2003/0233085 A1 | 12/2003 | Giammarusti |
| 2003/0236487 A1 | 12/2003 | Knowlton |
| 2004/0000316 A1 | 1/2004 | Knowlton et al. |
| 2004/0001809 A1 | 1/2004 | Brisken |
| 2004/0002705 A1 | 1/2004 | Knowlton et al. |
| 2004/0010222 A1 | 1/2004 | Nunomura et al. |
| 2004/0015106 A1 | 1/2004 | Coleman |
| 2004/0015559 A1 | 1/2004 | Goldstein |
| 2004/0030227 A1 | 2/2004 | Littrup |
| 2004/0039312 A1 | 2/2004 | Hillstead et al. |
| 2004/0039418 A1 | 2/2004 | Elstrom et al. |
| 2004/0049134 A1* | 3/2004 | Tosaya et al. .............. 601/2 |
| 2004/0059266 A1 | 3/2004 | Fry et al. |
| 2004/0073079 A1 | 4/2004 | Altshuler et al. |
| 2004/0073113 A1 | 4/2004 | Salgo |
| 2004/0073116 A1 | 4/2004 | Smith |
| 2004/0073204 A1 | 4/2004 | Ryan et al. |
| 2004/0077977 A1 | 4/2004 | Ella et al. |
| 2004/0082857 A1 | 4/2004 | Schonenberger et al. |
| 2004/0082859 A1 | 4/2004 | Schaer |
| 2004/0102697 A1 | 5/2004 | Evron |
| 2004/0105559 A1 | 6/2004 | Aylward et al. |
| 2004/0122493 A1 | 6/2004 | Ishbashi et al. |
| 2004/0143297 A1 | 7/2004 | Ramsey |
| 2004/0152982 A1 | 8/2004 | Hwang et al. |
| 2004/0186535 A1 | 9/2004 | Knowlton |
| 2004/0206365 A1 | 10/2004 | Knowlton |
| 2004/0210214 A1 | 10/2004 | Knowlton |
| 2004/0217675 A1 | 11/2004 | Desilets et al. |
| 2004/0249318 A1 | 12/2004 | Tanaka et al. |
| 2004/0254620 A1 | 12/2004 | Lacoste et al. |
| 2004/0267252 A1 | 12/2004 | Washington |
| 2005/0033201 A1 | 2/2005 | Takahashi et al. |
| 2005/0055073 A1 | 3/2005 | Weber |
| 2005/0070961 A1 | 3/2005 | Maki et al. |
| 2005/0074407 A1* | 4/2005 | Smith .............. 424/9.5 |
| 2005/0080469 A1 | 4/2005 | Larson |
| 2005/0091770 A1* | 5/2005 | Mourad et al. .............. 15/22.1 |
| 2005/0113689 A1 | 5/2005 | Gritzky |
| 2005/0137656 A1 | 6/2005 | Malak |
| 2005/0143677 A1 | 6/2005 | Young et al. |
| 2005/0154313 A1 | 7/2005 | Desilets et al. |
| 2005/0154314 A1 | 7/2005 | Quistgaard |
| 2005/0154332 A1 | 7/2005 | Zanelli |
| 2005/0154431 A1 | 7/2005 | Quistgaard |
| 2005/0187495 A1 | 8/2005 | Quistgaard et al. |
| 2005/0191252 A1 | 9/2005 | Mitsui |
| 2005/0193451 A1 | 9/2005 | Quistgaard et al. |
| 2005/0228281 A1 | 10/2005 | Nefos |
| 2005/0240170 A1 | 10/2005 | Zhang et al. |
| 2005/0256406 A1 | 11/2005 | Barthe |
| 2005/0261584 A1 | 11/2005 | Eshel et al. |
| 2005/0267454 A1 | 12/2005 | Hissong et al. |
| 2006/0004306 A1 | 1/2006 | Altshuler |
| 2006/0020260 A1 | 1/2006 | Dover et al. |
| 2006/0025756 A1 | 2/2006 | Francischelli |
| 2006/0042201 A1 | 3/2006 | Curry |
| 2006/0058664 A1 | 3/2006 | Barthe |
| 2006/0058671 A1 | 3/2006 | Vitek et al. |
| 2006/0058707 A1 | 3/2006 | Barthe |
| 2006/0058712 A1 | 3/2006 | Altshuler et al. |
| 2006/0074309 A1 | 4/2006 | Bonnefous |
| 2006/0074313 A1 | 4/2006 | Slayton |
| 2006/0074314 A1 | 4/2006 | Slayton |

(56) References Cited

U.S. PATENT DOCUMENTS

| | | |
|---|---|---|
| 2006/0074355 A1 | 4/2006 | Slayton |
| 2006/0079816 A1 | 4/2006 | Barthe |
| 2006/0079868 A1 | 4/2006 | Makin |
| 2006/0084891 A1 | 4/2006 | Barthe |
| 2006/0089632 A1 | 4/2006 | Barthe |
| 2006/0089688 A1 | 4/2006 | Panescu |
| 2006/0094988 A1 | 5/2006 | Tosaya et al. |
| 2006/0111744 A1 | 5/2006 | Makin |
| 2006/0116671 A1 | 6/2006 | Slayton |
| 2006/0122508 A1 | 6/2006 | Slayton |
| 2006/0122509 A1 | 6/2006 | Desilets |
| 2006/0161062 A1 | 7/2006 | Arditi et al. |
| 2006/0184069 A1 | 8/2006 | Vaitekunas |
| 2006/0184071 A1 | 8/2006 | Klopotek |
| 2006/0206105 A1 | 9/2006 | Chopra |
| 2006/0229514 A1 | 10/2006 | Wiener |
| 2006/0241440 A1 | 10/2006 | Eshel et al. |
| 2006/0241442 A1 | 10/2006 | Barthe |
| 2006/0250046 A1 | 11/2006 | Koizumi et al. |
| 2006/0261584 A1 | 11/2006 | Eshel |
| 2006/0282691 A1 | 12/2006 | Barthe |
| 2006/0291710 A1 | 12/2006 | Wang et al. |
| 2007/0032784 A1 | 2/2007 | Gliklich |
| 2007/0035201 A1 | 2/2007 | Desilets et al. |
| 2007/0055154 A1 | 3/2007 | Torbati |
| 2007/0055156 A1 | 3/2007 | Desilets et al. |
| 2007/0087060 A1 | 4/2007 | Dietrich |
| 2007/0088346 A1* | 4/2007 | Mirizzi et al. .......... 606/27 |
| 2007/0161902 A1 | 7/2007 | Dan |
| 2007/0167709 A1 | 7/2007 | Slayton |
| 2007/0208253 A1 | 9/2007 | Slayton |
| 2007/0239075 A1 | 10/2007 | Rosenberg et al. |
| 2008/0027328 A1 | 1/2008 | Klopotek et al. |
| 2008/0039724 A1 | 2/2008 | Seip et al. |
| 2008/0071255 A1 | 3/2008 | Barthe |
| 2008/0086054 A1 | 4/2008 | Slayton |
| 2008/0097253 A1 | 4/2008 | Pedersen |
| 2008/0167556 A1 | 7/2008 | Thompson et al. |
| 2008/0200813 A1 | 8/2008 | Quistgaard |
| 2008/0214966 A1 | 9/2008 | Slayton |
| 2008/0221491 A1 | 9/2008 | Slayton |
| 2008/0275342 A1 | 11/2008 | Barthe |
| 2008/0281237 A1 | 11/2008 | Slayton |
| 2008/0281255 A1 | 11/2008 | Slayton |
| 2008/0294073 A1 | 11/2008 | Barthe |
| 2008/0319356 A1 | 12/2008 | Cain et al. |
| 2009/0069677 A1 | 3/2009 | Chen et al. |
| 2009/0182231 A1 | 7/2009 | Barthe et al. |
| 2009/0216159 A1 | 8/2009 | Slayton et al. |
| 2009/0253988 A1 | 10/2009 | Slayton et al. |
| 2009/0318909 A1 | 12/2009 | Debenedictis et al. |
| 2010/0011236 A1 | 1/2010 | Barthe et al. |
| 2010/0022922 A1 | 1/2010 | Barthe et al. |
| 2010/0160782 A1 | 6/2010 | Slayton et al. |
| 2010/0241035 A1 | 9/2010 | Barthe et al. |
| 2010/0280420 A1 | 11/2010 | Barthe et al. |
| 2011/0112405 A1 | 5/2011 | Barthe et al. |
| 2011/0178444 A1 | 7/2011 | Slayton et al. |
| 2012/0016239 A1 | 1/2012 | Barthe et al. |
| 2012/0029353 A1 | 2/2012 | Slayton et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0111339 A1 | 5/2012 | Barthe et al. |
| 2012/0143056 A1 | 6/2012 | Slayton et al. |
| 2012/0165668 A1 | 6/2012 | Slayton et al. |
| 2012/0165848 A1 | 6/2012 | Slayton et al. |
| 2012/0197120 A1 | 8/2012 | Makin et al. |
| 2012/0197121 A1 | 8/2012 | Slayton et al. |
| 2012/0215105 A1 | 8/2012 | Slayton et al. |

FOREIGN PATENT DOCUMENTS

| | | |
|---|---|---|
| DE | 10219217 | 11/2003 |
| DE | 10219297 | 11/2003 |
| DE | 20314479 | 3/2004 |
| EP | 0344773 | 6/1989 |
| EP | 0344773 A2 | 12/1989 |
| EP | 0473553 A | 3/1992 |
| EP | 0473553 | 4/1992 |
| EP | 0661029 | 7/1995 |
| EP | 1050322 | 11/2000 |
| EP | 1234566 | 8/2002 |
| EP | 1262160 | 12/2002 |
| EP | 1479412 A1 | 11/2004 |
| GB | 2113099 | 8/1983 |
| JP | 63036171 | 2/1988 |
| JP | 03048299 | 3/1991 |
| JP | 3123559 | 5/1991 |
| JP | 03136642 | 6/1991 |
| JP | 4089058 | 3/1992 |
| JP | 7080087 | 3/1995 |
| JP | 07505793 | 6/1995 |
| JP | 7222782 | 8/1995 |
| JP | 09047458 | 2/1997 |
| JP | 11505440 | 5/1999 |
| JP | 2000166940 | 6/2000 |
| JP | 2001170068 | 6/2001 |
| JP | 2002078764 | 3/2002 |
| JP | 200252118 | 7/2002 |
| JP | 2002515786 | 8/2002 |
| JP | 2002537939 | 11/2002 |
| JP | 2003050298 | 2/2003 |
| JP | 2003204982 | 7/2003 |
| JP | 2004147719 | 5/2004 |
| JP | 2005503388 | 2/2005 |
| JP | 2005527336 | 9/2005 |
| JP | 2005323213 | 11/2005 |
| JP | 2006520247 | 9/2006 |
| JP | 2009518126 | 5/2009 |
| JP | 2010157695 | 5/2010 |
| KR | 1020010024871 | 3/2001 |
| KR | 100400870 B1 | 10/2003 |
| KR | 1020060113930 | 11/2006 |
| KR | 1020070065332 | 6/2007 |
| KR | 1020070070161 | 7/2007 |
| KR | 1020070098856 | 10/2007 |
| KR | 1020070104878 | 10/2007 |
| KR | 1020070114105 | 11/2007 |
| WO | 9625888 | 8/1996 |
| WO | WO9735518 | 10/1997 |
| WO | WO9832379 | 7/1998 |
| WO | WO9933520 | 7/1999 |
| WO | WO9949788 | 10/1999 |
| WO | 0006032 | 2/2000 |
| WO | 0015300 | 3/2000 |
| WO | WO0015300 | 3/2000 |
| WO | 0021612 | 4/2000 |
| WO | WO0021612 | 4/2000 |
| WO | 0053113 | 9/2000 |
| WO | 0128623 | 4/2001 |
| WO | WO0128623 | 4/2001 |
| WO | 0182777 | 11/2001 |
| WO | 0182778 | 11/2001 |
| WO | 0187161 | 11/2001 |
| WO | WO0182777 | 11/2001 |
| WO | WO0182778 | 11/2001 |
| WO | WO0187161 | 11/2001 |
| WO | 0209813 | 2/2002 |
| WO | WO0209813 | 2/2002 |
| WO | WO0224050 | 3/2002 |
| WO | WO02092168 | 11/2002 |
| WO | 03065347 | 8/2003 |
| WO | WO03070105 | 8/2003 |
| WO | WO03077833 | 9/2003 |
| WO | WO03086215 | 10/2003 |
| WO | 03096883 | 11/2003 |
| WO | 03099177 | 12/2003 |
| WO | 03101530 A2 | 12/2003 |
| WO | WO03099177 | 12/2003 |

(56) References Cited

FOREIGN PATENT DOCUMENTS

| WO | WO03101530 | 12/2003 |
|---|---|---|
| WO | 2004080147 | 9/2004 |
| WO | 2004110558 | 12/2004 |
| WO | 2005065408 | 7/2005 |
| WO | 2005090978 | 9/2005 |
| WO | 2006036870 | 4/2006 |
| WO | 2006042168 | 4/2006 |
| WO | 2006042201 | 4/2006 |
| WO | 2006065671 | 6/2006 |
| WO | 2006082573 | 8/2006 |
| WO | 2009013729 | 1/2009 |

OTHER PUBLICATIONS

Hassan et al, "Structure and Morphology of Freeze/Thawed PVA Hydrogels," Macromolecules, Mar. 11, 2000, pp. 2472-2479, vol. 33, No. 7.

Paradossi et al, "Poly(vinyl alcohol) as versatile biomaterial for potential biomedical applications," Journal of Materials Science: Materials in Medicine, 2003, pp. 687-691, vol. 14.

Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.

Barthe et al, "Ultrasound therapy system and ablation results utilizing miniature imaging/therapy arrays," Ultrasonics Symposium, 2004 IEEE, Aug. 23, 2004, pp. 1792-1795, vol. 3.

Makin et al, "Confirmal Bulk Ablation and Therapy Monitoring Using Intracorporeal Image-Treat Ultrasound Arrays," 4th International Symposium on Theraputic Ultrasound, Sep. 19, 2004.

Surry et al, "Poly(vinyl alcohol) cryogel phantoms for use in ultrasound and MR imaging," Phys. Med. Biol., Dec. 6, 2004, pp. 5529-5546, vol. 49.

Manohar et al, "Photoacoustic mammography laboratory prototype: imaging of breast tissue phantoms," Journal of Biomedical Optics, Nov./Dec. 2004, pp. 1172-1181, vol. 9, No. 6.

Mast et al, "Bulk Ablation of Soft Tissue with Intense Ultrasound: Modeling and Experiments," J. Acoust. Soc. Am. 2005, Oct. 1, 2005, pp. 2715-2724, vol. 118(4).

Makin et al, "Miniaturized Ultrasound Arrays for Interstitial Ablation and Imaging," UltraSound MEd. Biol. 2005, Nov. 1, 2005, pp. 1539-1550, vol. 31(11).

White et al, "Selective Creation of Thermal Injury Zones in the Superficial Musculoaponeurotic System Using Intense Ultrasound Therapy," Arch Facial Plastic Surgery, Jan./Feb. 2007, vol. 9, No. 1.

Gliklich et al, "Clinical Pilot Study of Intense Ultrasound Therapy to Deep Dermal Facial Skin and Subcutaneous Tissues," Arch Facial Plastic Surgery, Mar. 1, 2007, vol. 9, No. 2.

International Search Report and Written Opinion dated Aug. 20, 2008.

Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.

Wasson, Scott, "NVIDIA's GeFroce 7800 GTX graphics processor Power MADD," http://techreport.com/reviews/2005q2/geforce-7800gtx/index.x?pg=1, Jun. 22, 2005, 4 pages.

Coon, Joshua et al., "Protein identification using sequential ion/ion reactions and tandem mass spectometry" Proceedings of the National Academy of Sciences of the USA, vol. 102, No. 27, Jul. 5, 2005, pp. 9463-9468.

Corry, Peter M., et al., "Human Cancer Treatment with Ultrasound", IEEE Transactions on Sonics and Ultrasonics, vol. SU-31, No. 5, Sep. 1984, pp. 444,456.

Daum et al., "Design and Evaluation of a Feedback Based Phased Array System for Ultrasound Surgery," IEEE Transactions on Ultrasonics, Feroelectronics, and Frequency Control, vol. 45, No. 2, Mar. 1998, pp. 431-438.

Davis, Brian J., et al., "An Acoustic Phase Shift Technique for the Non-Invasive Measurement of Temperature Changes in Tissues", 1985 Ultrasonics Symposium, pp. 921-924.

Sassen, Sander, "ATI's R520 architecture, the new king of the hill?" http://www.hardwareanalysis.com/content/article/1813, Sep. 16, 2005, 2 pages.

Husseini et al, "The Role of Cavitation in Acoustically Activated Drug Delivery," J. Control Release, Oct. 3, 2005, pp. 253-261, vol. 107(2).

Husseini et al. "Investigating the mechanism of accoustically activated uptake of drugs from Pluronic micelles," BMD Cancer 2002, 2:20k, Aug. 30, 2002, pp. 1-6.

Wang, H., et al., "Limits on Focused Ultrasound for Deep Hyperthermia", 1994 Ultrasonic Symposium, Nov. 1-4, 1994, pp. 1869-1872, vol. 3.

Ueno, S., et al., "Ultrasound Thermometry in Hyperthermia", 1990 Ultrasonic Symposium, pp. 1645-1652.

Jenne, J., et al., "Temperature Mapping for High Energy US-Therapy", 1994 Ultrasonics Symposium, pp. 1879-1882.

Johnson, S.A., et al., "Non-Intrusive Measurement of Microwave and Ultrasound-Induced Hyperthermia by Acoustic temperature Tomography", Ultrasonics Symposium Proceedings, pp. 977-982.

Syka J. E. P. et al., "Peptide and Protein Sequence Analysis by Electron Transfer Dissociation Mass Spectometry," Proceedings of the National Academy of Sciences of USA, National Academy of Aceince, Washington, DC, vol. 101, No. 26, Jun. 29, 2004, pp. 9528-9533.

Mitragotri, Samir; "Healing sound: the use of ultrasound in drug delivery and other therapeutic applications," Nature Reviews; Drug Delivery, pp. 255-260, vol. 4.

Smith, Nadine Barrie, et al., "Non-Invasive In Vivo Temperature Mapping of Ultrasound Heating Using Magnetic Resonance Techniques", 1994 Ultrasonics Symposium, pp. 1829-1832, vol. 3.

Sanghvi, N. T., et al., "Transrectal Ablation of Prostate Tissue Using Focused Ultrasound," 1993 Ultrasonics Symposium, IEEE, pp. 1207-1210.

Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.

Seip, Ralf, et al., "Noninvasive Detection of Thermal Effects Due to Highly Focused Ultrasonic Fiels," IEEE Symposium, pp. 1229-1232, vol. 2, Oct. 3-Nov. 1993.

Reid, Gavin, et al., "Tandem Mass spectrometry of ribonuclease A and B: N-linked glycosylation site analysis of whole protein ions," Analytical Chemistry. Feb. 1, 2002, vol. 74, No. 3, pp. 577-583.

Righetti et al, "Elastographic Characterization of HIFU-Induced Lesions in Canine Livers," 1999, Ultrasound in Med & Bio, vol. 25, No. 7, pp. 1099-1113.

Written Opinion of PCT/US2008/062932 dated Aug. 20, 2008.

PCT/US2012/046122 International Search Report Jan. 30, 2013.

PCT/US2012/046123 International Search Report Jan. 28, 2013.

PCT/US2012/046125 International Search Report Jan. 28, 2013.

Chen, L. et al., ""Effect of Blood Perfusion on the ablation of liver perenchyma with high intensity focused ultrasound,"" Phys. Med. Biol; 38:1661-1673; 1993b.

Damianou et al., Application of the Thermal Dose Concept for Predicting the Necrosed Tissue Volume During Ultrasound Surgery, 1993 IEEE Ultrasound Symposium, pp. 1199-1202.

Fry, W.J. et al., "Production of Focal Destructive Lesions in the Central Nervous System with Ultrasound," J. Neurosurg., 11:471-478; 1954.

Harr, G.R. et al., "Tissue Destruction with Focused Ultrasound in Vivo," Eur. Urol. 23 (suppl. 1):8-11; 1993.

Jeffers et al., "Evaluation of the Effect of Cavitation Activity on Drug-Ultrasound Synergisms," 1993 IEEE Ultrasonics Symposium, pp. 925-928.

Madersbacher, S. et al., "Tissue Ablation in Bening Prostatic Hyperplasia with High Intensity Focused Ultrasound," Dur. Urol., 23 (suppl. 1):39-43; 1993.

Saad et al., "Ultrasound-Enhanced Effects of Adriamycin Against Murine Tumors," Ultrasound in Med. & Biol. vol. 18, No. 8, pp. 715-723 (1992).

(56) References Cited

OTHER PUBLICATIONS

Simon et al., "Applications of Lipid-Coated Microbubble Ultrasonic Contrast to Tumor Therapy," Ultrasound in Med. & Biol. vol. 19, No. 2, pp. 123-125 (1993).

Talbert, D. G., "An Add-On Modification for Linear Array Real-Time Ultrasound Scanners to Produce 3D Displays," UTS Int'l 1977 Brighton, England (Jun. 28-30, 1977) pp. 57-67.

Tata et al., "Interaction of Ultrasound and Model Membrane Systems: Analyses and Predictions," American Chemical Society, Phys. Chem. 1992, 96, pp. 3548-3555.

International Preliminary Report on Patentability for International application No. PCT/US2008/062932 dated Nov. 19, 2009.

Arthur et al., "Non-invasive estimation of hyperthermia temperatures with ultrasound," Int. J. Hyperthermia, Sep. 2005, 21(6), pp. 589-600.

* cited by examiner

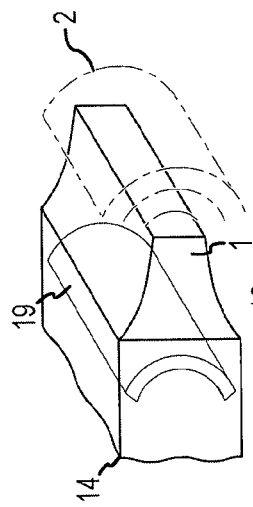
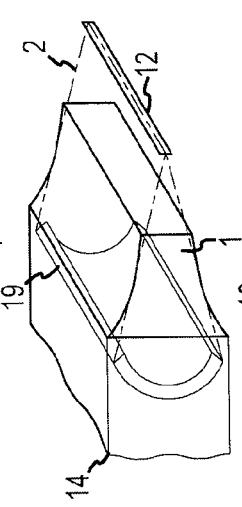
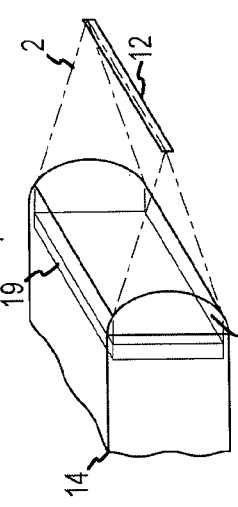
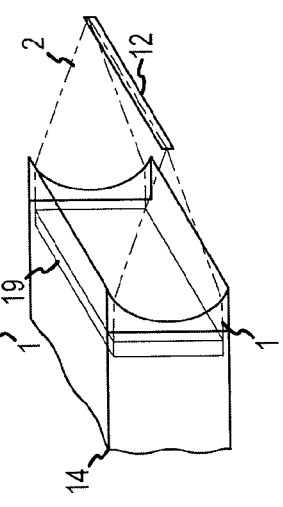
FIG.2f  FIG.2g  FIG.2h  FIG.2i
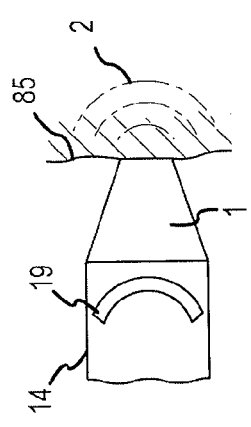
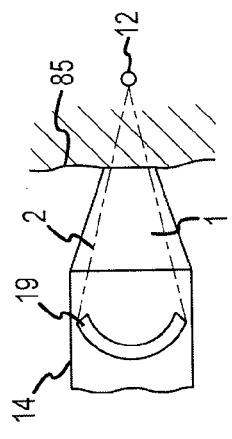
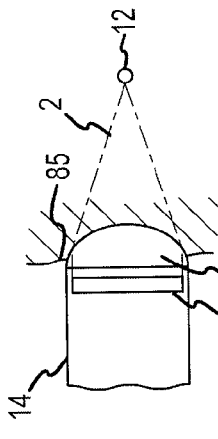
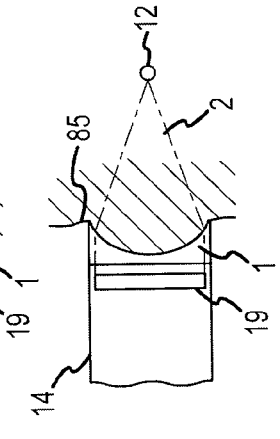
FIG.2b  FIG.2c  FIG.2d  FIG.2e

METHODS AND SYSTEMS FOR COUPLING AND FOCUSING ACOUSTIC ENERGY USING A COUPLER MEMBER

CROSS-REFERENCE TO RELATED APPLICATIONS

This application claims the benefit of U.S. Provisional Patent Application Ser. No. 60/916,502, entitled METHODS AND SYSTEMS FOR COUPLING ACOUSTIC ENERGY USING A GEL FILLED LENS, filed May 7, 2007, which is incorporated by reference herein in its entirety.

BACKGROUND OF THE INVENTION

Ultrasound has long been used for diagnostic imaging applications. More recently however, several new therapeutic applications for ultrasound are being discovered. Ultrasound therapy typically uses an ultrasound transducer to radiate acoustic energy to a treatment region. Ultrasound transducers typically comprise at least one transduction element configured to focus or defocus acoustic energy. To suitably focus or defocus acoustic energy to a treatment region, the geometry of the ultrasound transduction element(s) is adjustably configured (e.g., concave, convex, and/or planar). Alternatively, or additionally, ultrasound transducers may comprise one or more adjustably configured lenses to appropriately focus or defocus acoustic energy.

Because acoustic energy is poorly transmitted through air, it is important that it be effectively coupled to the treatment region and that the couple is acoustically transparent. To achieve acoustic transparency, the couple is typically similar in acoustic properties to the cells and/or tissues within the treatment region. Typically, a fluid or a gel is used as the couple, with such fluid or gel spread along the outer surface, such as the epidermis layer, in between the transducer probe and the outer surface to facilitate acoustic coupling.

SUMMARY OF THE INVENTION

In accordance with exemplary embodiments, this invention improves upon the prior art by providing a coupler member configured to perform at least one of (i) providing a standoff, (ii) focusing or defocusing energy, and (iii) coupling energy. In accordance with various aspects of exemplary embodiments, the coupler member is fluid filled, gel filled, gel, or solid. In an exemplary embodiment, the energy is acoustic energy (e.g., ultrasound). In other exemplary embodiments, the energy is photon based energy (e.g., IPL, LED, laser, white light, etc.), or other energy forms, such radio frequency electric currents, or various combinations of acoustic energy, electromagnetic energy and other energy forms or energy absorbers such as cooling.

In accordance with one exemplary embodiment, this invention discloses an encapsulated, substantially acoustically transparent fluid filled coupler member, wherein the encapsulation provides a standoff and couples acoustic energy. In accordance with another exemplary embodiment, this invention discloses a substantially acoustically transparent gel coupler member, wherein the gel is configured to provide a standoff, hold the shape of a lens geometry, and couple acoustic energy.

In accordance with one aspect of the present invention, an exemplary gel coupler member comprises water, glycerol, and polyvinyl alcohol, and exhibits an increased desiccation time and shelf life when compared to the prior art. In one embodiment, an acoustically transparent gel coupler member may be adjustably configured to hold the shape of a lens geometry by forming it in a mold or shell.

An exemplary system for coupling acoustic energy using a coupler member comprises a control system, a probe, a coupler member, as mentioned above, and a display or indicator system. The probe can comprise various probe and/or transducer configurations. In an exemplary embodiment, the probe delivers focused, unfocused, and/or defocused ultrasound energy to the region of interest. Imaging and/or monitoring may alternatively be coupled and/or co-housed with an ultrasound system contemplated by the present invention.

The control system and display system can also comprise various configurations for controlling probe and system functionality, including for example, a microprocessor with software and a plurality of input/output devices, a system for controlling electronic and/or mechanical scanning and/or multiplexing of transducers, a system for power delivery, systems for monitoring, systems for sensing the spatial position of the probe and/or transducers, and systems for handling user input and recording treatment results, among others.

BRIEF DESCRIPTION OF THE DRAWINGS

The subject matter of the invention is particularly pointed out and distinctly claimed in the concluding portion of the specification. The invention, however, both as to structure and method of operation, may best be understood by reference to the following description taken in conjunction with the claims and the accompanying drawing figures, in which like parts may be referred to by like numerals, and:

FIGS. 2B-2K illustrate various fluid filled and gel coupler members in accordance with exemplary embodiments of the present invention;

DETAILED DESCRIPTION

The present invention may be described herein in terms of various functional components and processing steps. It should be appreciated that such components and steps may be realized by any number of hardware components configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of medical contexts and the exemplary embodiments relating to methods and systems for coupling acoustic energy using a coupler member, as described herein, are merely indicative of exemplary applications for the invention. For example, the principles, features and methods discussed may be applied to any medical application. Further, various aspects of the present invention may be suitably applied to other applications.

In accordance with exemplary embodiments, this invention provides a coupler member configured to perform at least one of (i) providing a standoff, (ii) focusing or defocusing energy, and (iii) coupling energy. In accordance with various aspects of exemplary embodiments, the coupler member is fluid filled, gel filled, gel, or solid.

In exemplary embodiments, a fluid filled coupler member is comprised of a fluid within an encapsulation. The fluid may be water, aqueous solutions, organic solvents including alcohols, dimethyl sulfoxide, oils, monomeric or polymeric polyols, siloxanes or polysiloxanes, perfluorocarbon liquids, and mixtures thereof. In an exemplary embodiment, the fluid has a low viscosity; however, the fluid has a high viscosity in other embodiments. The encapsulation may be comprised of a plastic, an elastomeric material, a laminate or a thin metal layer, and combinations thereof.

Figure 1A:
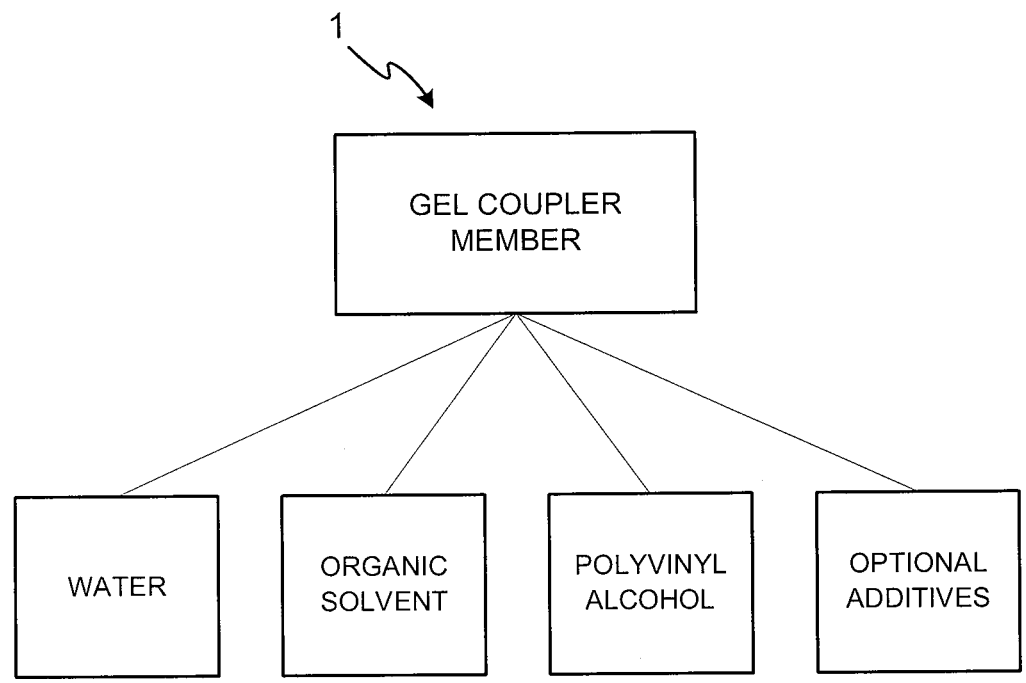
FIG. 1A illustrates a block diagram of a coupler member formulation in accordance with an exemplary embodiment of the present invention.

In exemplary embodiments, a gel coupler member comprises a thick fluid, gel or a solid formulation. While various compositions are disclosed, any formulation having good acoustic properties (low attenuation), desiccation time and/or shelf life is suitable for use within the coupler member. As depicted in FIG. 1A, in some embodiments, a gel coupler member 1 comprises water, an organic solvent, and polyvinyl alcohol (PVA). Without being limited to any theory, it is believed that PVA cryogels made with organic solvents have a finer structure than gels made only with water, have lower ultrasound attenuation due to scattering, and do not expand during the freezing cycle.

While the PVA gel formulation is described herein as comprising water, any solvent in which PVA or the organic solvent is soluble may be used. For example, deionized water, aqueous buffer solutions such as phosphate buffer solution, methanol, ethanol, organic solvents such as dimethyl sulfoxide, and mixtures thereof, may be used.

In some embodiments, the organic solvent is glycerol. Glycerol is attractive because it is biocompatible and hygroscopic. Glycerol also promotes gelation in PVA solutions even without freeze-thaw cycles. However, the organic solvent may be any solvent compatible with water. For example, dimethyl sulfoxide might be used, combined with phonophoresis, as a drug transport mechanism. Other suitable organic solvents include acetone, methyl alcohol, ethyl alcohol, n-propyl alcohol, iso-propyl alcohol, aminoethyl alcohol, phenol, tetrahydrofuran, dimethyl formamide, glycerine, ethylene glycol, propylene glycol, poly-ethylene glycol, and triethylene glycol.

Moreover, while the gel formulation is described herein as comprising PVA, other polymers may be used. For example, polyacrylamide, poly(vinyl acetate), poly(vinyl butyral), poly(vinyl pyrrolidone), poly(2-hydroxyethyl methacrylate) and mixtures thereof, may be used.

In some embodiments, the gel coupler member formulation comprises optional additives. For example, the formulation may comprise a medicant, an anesthetic, a calcification inhibitor, a bioactive agent, a dopant, a coloring agent (e.g., a dye), a water softening agent (e.g., a builder or chelating agent), a pH modifier, a preservative, an odor absorber, a viscosity modifier, a neutralizer, a cationic conditioning polymer, an antibacterial agent or biocide such as benzalkonium chloride, a vitamin, a botanical extract, a skin conditioner (e.g. an ester), a moisturizer (e.g., a humectant) and or mixtures thereof.

In an exemplary embodiment, the thick fluid or gel coupler member contains medicines and other drugs that are delivered to a region of interest during the emission of energy from the probe.

In exemplary embodiments, the gel coupler member formulation comprises water in an amount of from about 10% to about 90% percent mass or more preferably from about 30% to about 50% percent mass, an organic solvent in an amount of from about 10% to about 90% percent mass or more preferably from about 40% to about 60% percent mass, PVA in an amount of up to about 30% or more preferably from about 2% to about 20% percent mass, wherein the PVA is at least 90% hydrolyzed and the molecular weight is between about 70,000 and 120,000, and optional additives in an amount of from about 0.1% to about 2% percent mass of the gel coupler member formulation. In some embodiments, the PVA is more than 99% hydrolyzed and the degree of polymerization is about 1800 to about 2300. Table 1 summarizes an exemplary formulation of a PVA gel.

TABLE 1

| | Water | Glycerol | PVA (99+ % hydrolyzed, MW = 89,000 to 98,000) | Benzalkonium chloride as a biocide |
|---|---|---|---|---|
| % mass | 40.7% | 51.2% | 8.1% | 0.1% |

The gel coupler member formulation can be prepared by dissolving PVA at an elevated temperature in a mixed solvent comprising water and the organic solvent, followed by crystallization of PVA at temperatures below room temperature. In exemplary embodiments, two freeze-thaw cycles produce gels with good mechanical properties. Notwithstanding, more or less that two freeze-thaw cycles may be used. Indeed, in some embodiments, no freeze-thaw cycles are needed. In addition, the organic solvent may be removed from the gel by washing for an extended amount of time in water; the resulting high water content gel having a speed of sound closer to tissue.

In some embodiments, irradiation (e.g., covalent crosslinking) sterilizes gel coupler member formulations and/or provides formulations with improved transparency (e.g., acoustic and/or optical), mechanical properties, thermal resistance, and/or dimensional stability. After irradiation, physical associations may optionally be removed by heating. A coupler member in accordance with some embodiments has a melting point of about 70 C. The gel coupler member formulations described herein are porous in some embodiments. In some embodiments, the visible light transmission of the formulations described herein is above 80%.

In exemplary embodiments, the invention provides for gel coupler member formulations substantially free from bubbles. In exemplary embodiments, obtaining gel coupler member formulations substantially free from bubbles comprises vacuum degassing of the heated liquid prior to gel formation.

In exemplary embodiments, a gel coupler member is adjustably configured to hold the shape of a lens geometry to focus or defocus acoustic energy. In the preparation process for example, the gel formulation may be cast in one or more molds or shells and crystallized therein. The PVA gel may be crystallized (e.g, physically crosslinked) by repeated freeze-thaw cycles. The mold may be any appropriate shape and in exemplary embodiments, holds the shape of a lens geometry.

The shape of the gel coupler member may be configured as convex, concave, planar, cone and/or compound, comprising multiple lens shapes, to achieve focused, unfocused, or non-focused energy for imaging and/or therapy. Other lens shapes can still be used in other exemplary embodiments of the present invention. For example, any configuration is appropriate that ensures that a focal region of acoustic energy and/or imaging is disposed proximate a region of interest. In general, the lens shape will depend on the speed of sound in the material. In accordance with various embodiments, an additional lens may be embedded within the gel coupler member to provide increased focus adjustability. Moreover, non-homogenous gel coupler members may be formed to provide increased focus adjustability.

Figure 2A:
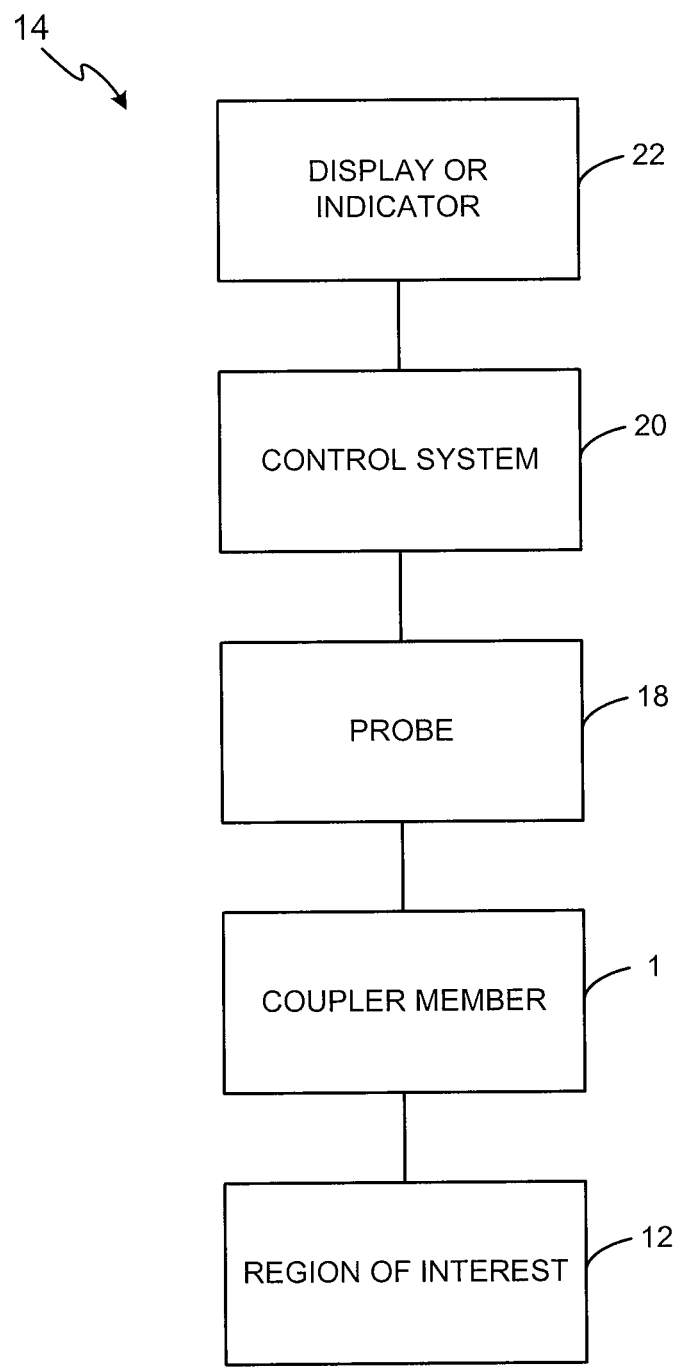
FIG. 2A illustrates a block diagram of a system incorporating a coupler member in accordance with an exemplary embodiment of the present invention.
Figure 2J:
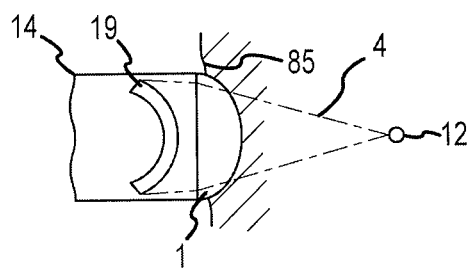
Figure 2K:
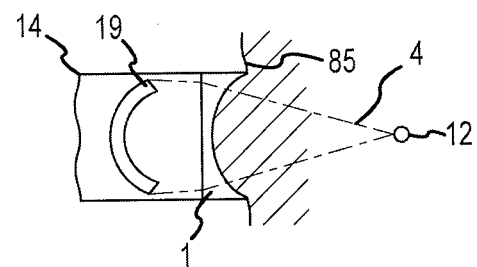
Figure 2L:
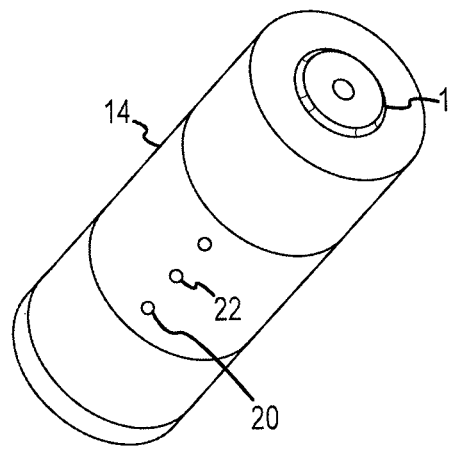
FIGS. 2L-2M illustrate various gel coupler members in accordance with exemplary embodiments of the present invention.
Figure 2M:
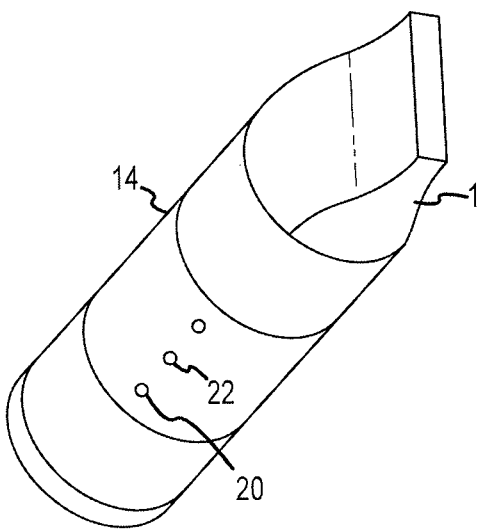
Figure 2N:
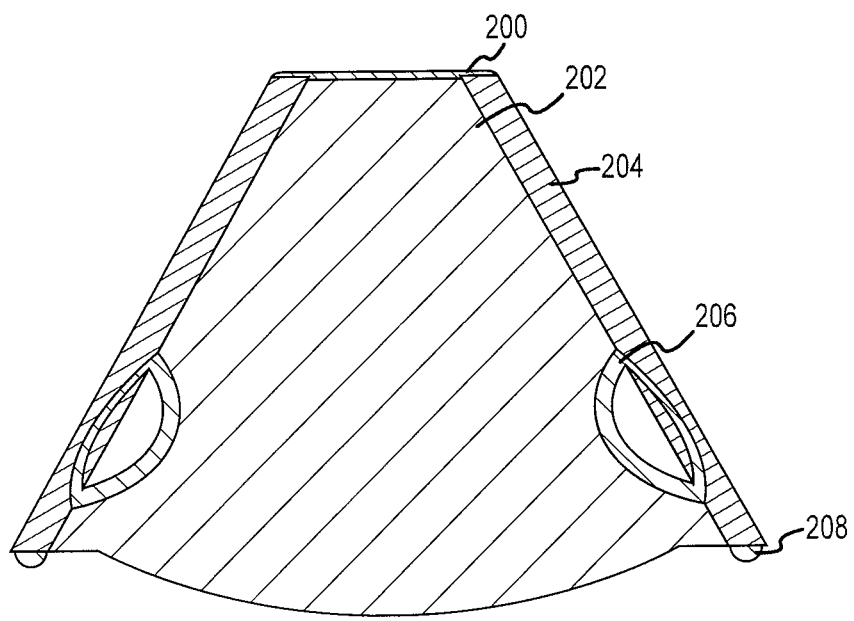
FIG. 2N illustrates an exemplary limited use gel coupler member in accordance with exemplary embodiments of the present invention.

In accordance with some embodiments, the mold or shell functions as a gel coupler member storage device, as shown in FIG. 2N. In some embodiments, a gel coupler member formulation 202 is sealed into a hard plastic shell 204 with low permeability. Shell 204 may include a mechanism to compensate for some desiccation, such as an elastomeric volume compensator 206. In this regard, gel coupler member formulation 202 is able to stay in contact with a membrane 200, where acoustic output occurs, as well as the transducer or probe housing. In some embodiments, a seal 208, shell 204 and membrane 200 are comprised of a plastic, an elastomeric material, a laminate or a thin metal layer, or combinations thereof. However, skilled artisans will appreciate that any material suitable for sealing gel coupler member formulation 202 is within the scope of the invention. In some applications, the gel coupler member will need to be shipped and stored in "high-barrier" packaging. When shipped and stored as disclosed herein, a gel coupler member, in accordance with the invention, can have a shelf life of at least several months.

In exemplary embodiments, a coupler member acts as an acoustically transparent coupling between the couple and one or both of the tissue and the energy source. In some embodiments, an additional coupling is necessary and/or multiple coupler members, each having distinct acoustic properties, are used. In one embodiment, an acoustically transparent coupling may be adjustably configured to hold the shape of a lens geometry by freezing. Syneresis (solvent exclusion) may provide a slippery surface for additional coupling.

In exemplary embodiments, a coupler member acts as a standoff to for example, compensate for a focal point at a fixed distance. In accordance with one exemplary embodiment, the couple is acoustically transparent. In accordance with another exemplary embodiment, the couple is acoustically non-transparent, but with preconceived acoustic properties, for example, to vary the acoustic energy. At least a portion of the coupler member coupling according to the invention is flexible and can adjust to the contours of a tissue surface.

In some embodiments, the coupler member can be used in multiple imaging and/or therapy applications. In other embodiments, the coupler member is a single-use or limited use, disposable device. In an exemplary embodiment, the couple can be a solid, such as ice, whereby a cooling effect can be imparted, or can be any other solid medium. In other exemplary embodiments, the couple can be a heated, such as via resistive or peltier devices and or cooled via peltier or other cooling means, including closed-loop control means of thermal regulation.

In accordance with exemplary embodiments, a part of a coupler member is configured for attachment to a probe. In some other embodiments, a mold or shell for a gel coupler member has an attachment portion for fitting to a probe, or an attachment device is embedded, and thereby fixed, in the gel coupler member formulation. In general, any mechanism for attachment is suitable and may include sleeves, brackets, clips, magnetism, or other means known in the art or hereinafter developed. In some embodiments, one or more clips will hold a mold or shell for a gel coupler member against the probe housing and simultaneously compress the seal against the probe housing.

The method of coupling acoustic energy using a coupler member comprises delivering energy to a region of interest (ROI) within one or more layers of tissue. In an exemplary embodiment, the energy is acoustic energy (e.g., ultrasound in the range of about 0.5 to about 20 MHz). In other exemplary embodiments, the energy is photon based energy (e.g., IPL, LED, laser, white light, etc.), or other energy forms, such radio frequency electric currents, or various combinations of acoustic energy, electromagnetic energy and other energy forms or energy absorbers such as cooling.

Figure 1B:
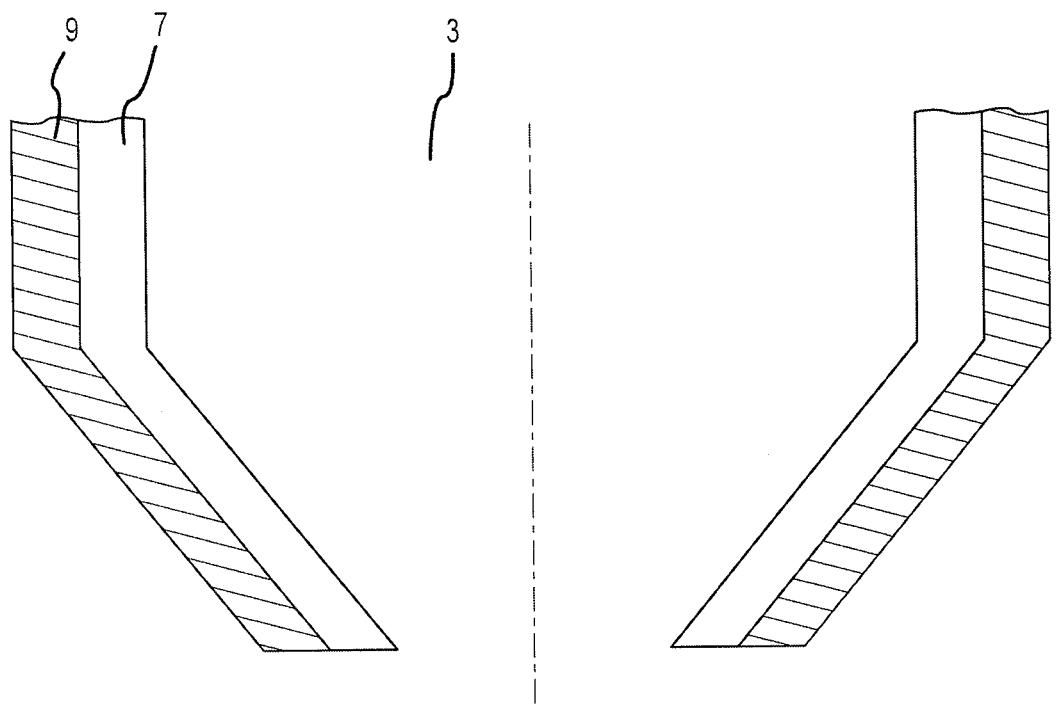
FIG. 1B illustrates a system in accordance with an exemplary embodiment of the present invention configured to accommodate a plurality of energy forms.

While the description generally refers to acoustic energy for convenience, it should be understood that the methods and systems described herein are likewise applicable to other energy forms. For example, in some embodiments, couples configured for photon-based energy are optically transparent, while in other embodiments, couples configured for RF or microwave are configured with electrodes or antennas. Moreover, the methods and systems described herein may accommodate a plurality of energy forms, and in some embodiments, for simultaneous operation, as depicted in FIG. 1B, wherein reference numeral 3 depicts acoustic energy delivery, sensing and imaging, 7 depicts photon based energy delivery, optical sensing and imaging, and 9 depicts electric energy delivery, sensing and imaging, the latter such as RF electric current energy, and electric impedance sensing and imaging.

For example, an exemplary system for coupling acoustic energy, sensing, and/or monitoring with photon-based and/or radio frequency energy, sensing, and/or monitoring comprises: a substantially acoustically transparent gel coupler member configured to hold the shape of a lens geometry; an optical waveguide; and electric contacts. Specifically, and with continued reference to FIG. 1B, an exemplary system comprises an optical waveguide 7 (e.g., clear glass or plastic) disposed next to a gel coupler member 3, and two electric contacts 9 which could pass bipolar (or e.g., monopolar) radio frequency current.

An exemplary system 14 for coupling acoustic energy using a coupler member is provided and depicted in FIG. 2A. An exemplary system 14 comprises a display or indicator 22, a control system 20, a probe 18, and a coupler member 1. Between gel coupler member 1 and ROI 12 an acoustic coupling agent, such as ultrasound coupling gel, or medicant may be employed in a preferred embodiment. Such additionally disposed coupling agent may be cooled or heated to impart additional control of therapy energy delivery.

Display system can be any type of system that conveys images or information apart from images about system 14 or ROI 12 to the user. Therefore, display system 22 can be a computer monitor, television screen or it can be a simply type of indicator system such a liquid crystal display or light emitting diode display in various exemplary embodiments. Liquid crystal displays and light emitting diode displays are particularly useful when system 14 is a hand-held system.

In various exemplary embodiments, ROI 12 is located within one of the nonviable epidermis (i.e., the stratum corneum), the viable epidermis, the dermis, the subcutaneous connective tissue and fat, and the muscle. Further, while only one ROI 12 is depicted, a plurality of ROI 12 can be treated, and in some embodiments, simultaneously. For example, ROI 12 may consist of one or more organs or a combination of tissues either superficial or deep within the body. In an exemplary embodiment ultrasound, photon based or radio frequency (electromagnetic) treatment is provided to artificial or engineered tissues, such as artificial skin or organs, or stem cell derived tissues.

Exemplary systems 14 are depicted in FIGS. 2B-2K, wherein each comprises a transducer 19 configured to emit energy 2 through a coupler member 1 at a ROI 12 below stratum corneum 85. In particular, FIGS. 2B, 2C, 2F, and 2G depict an encapsulated, acoustically transparent fluid filled coupler member 1, wherein the encapsulation provides a standoff and couples energy 2, while FIGS. 2D, 2E, and 2H-2K depict an acoustically transparent gel coupler member 1, wherein couple 1 is configured to provide a standoff, hold the shape of a lens geometry, and couple energy 2.

One skilled in the art will also appreciate that with reference to FIGS. 2D, 2E, and 2H-2K, coupler member 1 may be configured to focus energy (as shown), unfocus, and/or defocus energy, depending on the speed of sound through coupler member 1 as compare to that through the tissue surrounding ROI 12.

For example, coupler member 1 in FIGS. 2D and 2H will focus energy (as shown) if the speed of sound through coupler member 1 is less than that through the tissue surrounding ROI 12. Alternatively, coupler member 1 in FIGS. 2D and 2H will defocus energy if the speed of sound through coupler member 1 is greater than that through the tissue surrounding ROI 12. In yet another exemplary embodiment, coupler member 1 is configured to unfocus energy.

Similarly, coupler member 1 in FIGS. 2E and 2I will focus energy (as shown) if the speed of sound through coupler member 1 is greater than that through the tissue surrounding ROI 12. And alternatively, coupler member 1 in FIGS. 2E and 2I will defocus energy if the speed of sound through coupler member 1 is less than that through the tissue surrounding ROI 12. In yet another exemplary embodiment, coupler member 1 is configured to unfocus energy.

In accordance with exemplary embodiments, and with reference to FIGS. 2J and 2K, the focusing, unfocusing, and/or defocusing of transducer 19 and coupler member 1 may be additive or subtractive one with another.

In accordance with various exemplary embodiments, and as depicted in FIGS. 2L-2M, system 14 is configured to be held in and operated by a single hand of a user. System 14 comprises a display or indicator 22, a control system 20, a probe (not shown), and a coupler member 1. In an exemplary embodiment, system 14 weighs less than 800 g, and in more preferred embodiments, weighs less than 400 g.

Figure 3:
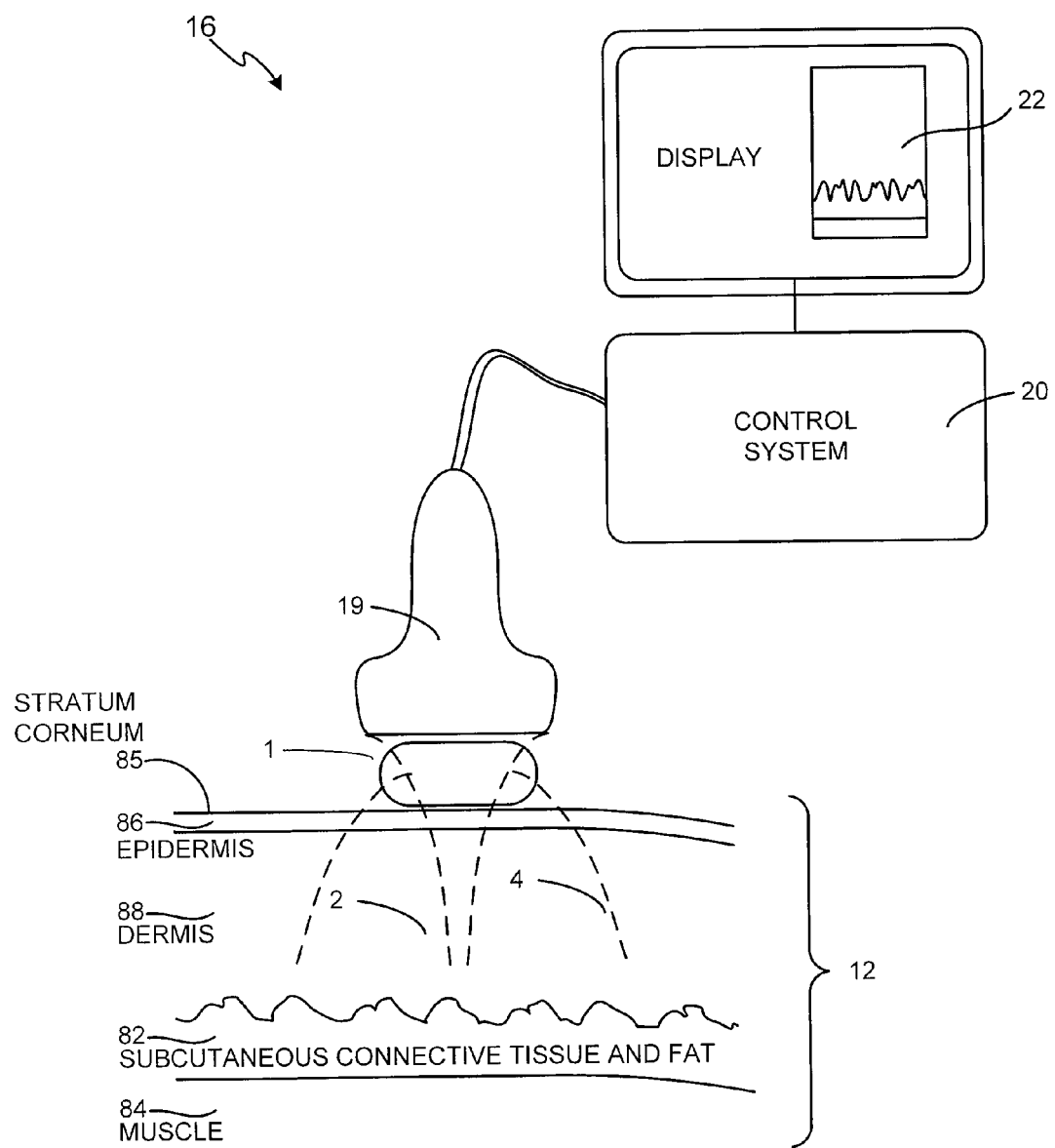
FIG. 3 illustrates a schematic diagram of a system incorporating a coupler member in accordance with an exemplary embodiment of the present invention.

In an exemplary embodiment, with reference to FIG. 3, an exemplary system 16, comprising a display 22, a control system 20, a transducer 19, and a coupler member 1 is used to deliver energy 2 and/or 4 to and monitor ROI 12, within one or more of stratum corneum 85, viable epidermis 86, dermis 88, subcutaneous connective tissue and fat 82, and muscle 84. Other exemplary systems are disclosed in co-pending U.S. patent application Ser. No. 10/950,112 entitled "Method and System For Combined Ultrasound Treatment", which is hereby incorporated by reference.

With continued reference to FIG. 3, an exemplary transducer 19 is a transducer that delivers ultrasound energy 2 and/or 4 to ROI 12. In some embodiments, coupler member 1 is used to couple transducer 19 to a patient's body. In some embodiments, an additional coupling is necessary and/or multiple coupler members 1 are used, each having distinct acoustic properties.

In another exemplary embodiment, suction is used to attach transducer 19 to the patient's body. In this exemplary embodiment, a negative pressure differential is created and transducer 19 attaches to stratum corneum 85 by suction. A vacuum-type device is used to create the suction and the vacuum device can be integral with, detachable, or completely separate from transducer 19. The suction attachment of transducer 19 to stratum corneum 85 and associated negative pressure differential ensures that transducer 19 is properly coupled to stratum corneum 85. Further, the suction-attachment also reduces the thickness of the tissue to make it easier to reach distinct layers of tissue.

With additional reference to FIG. 3, ultrasound energy 2 and/or 4 can be emitted in various energy fields. Energy fields can be focused, unfocused, defocused, and/or made substantially planar by transducer 19 to provide a plurality of different effects. Energy can be applied at one or more points in one or more C-planes or C-scans by automated or manual movement. For example, a substantially planar energy field can provide a therapeutic and/or pretreatment effect, a focused energy field can provide a more intense therapeutic effect, and a non-focused energy field can provide a more mild therapeutic effect. It should be noted that the term "non-focused" as used throughout, is meant to encompass energy that is unfocused or defocused.

An exemplary transducer 19 emits ultrasound energy for imaging, or treatment, or a combination of both imaging and treatment. In an exemplary embodiment, transducer 19 is configured to emit ultrasound energy at specific depths in ROI 12, as described below. In this exemplary embodiment of FIG. 3, transducer 19 emits unfocused or defocused ultrasound energy over a wide area in ROI 12 for treatment purposes.

Figure 4A:
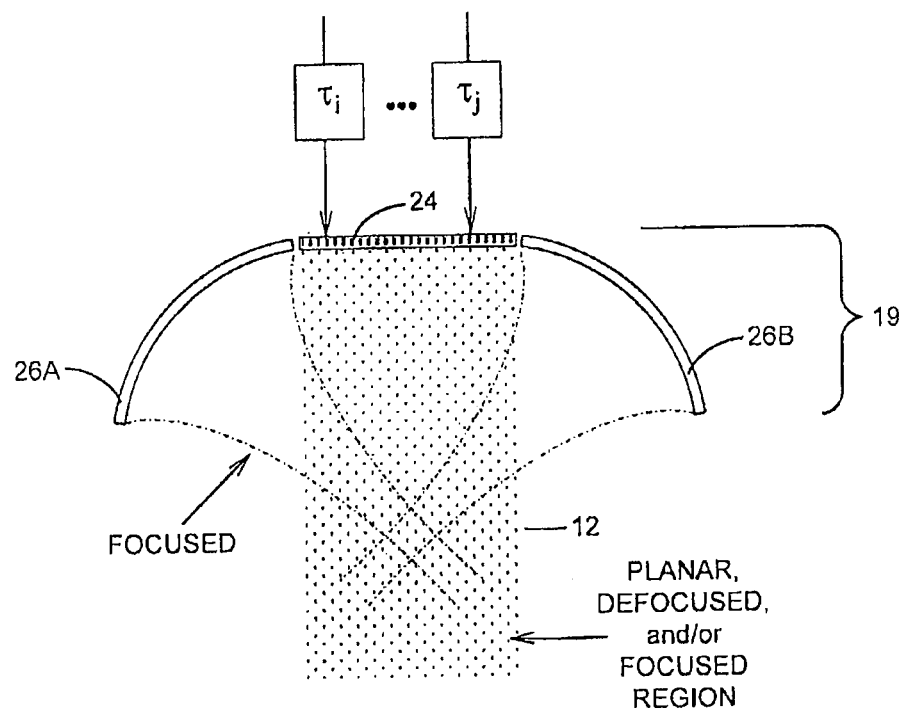
FIGS. 4A, 4B, 4C, 4D and 4E illustrate cross-sectional diagrams of an exemplary transducer in accordance with various embodiments of the present invention.
Figure 4B:
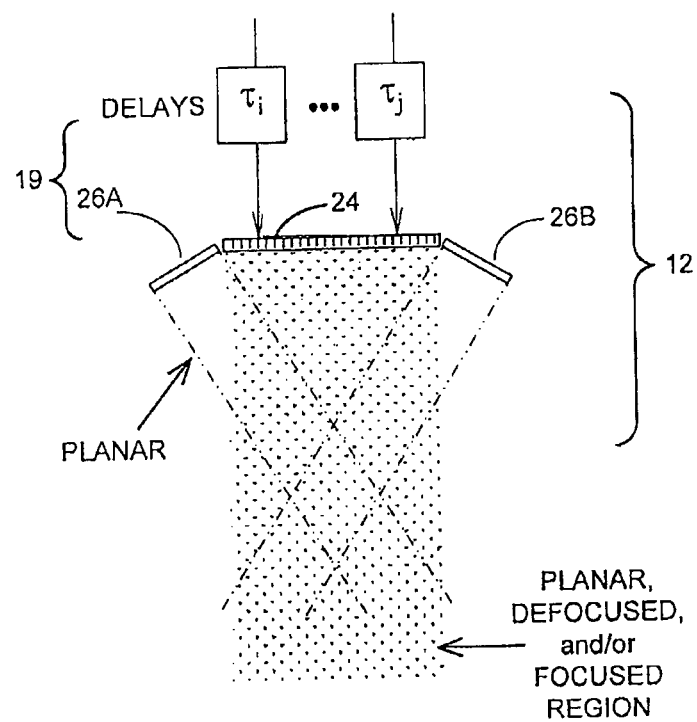

With reference to FIGS. 4A and 4B, transducer 19 can comprise one or more transducers configured for facilitating treatment. Transducer 19 can also comprise one or more transduction elements, e.g., elements 26A or 26B. The transduction elements can comprise a piezoelectrically active material, such as lead zirconante titanate (PZT), or any other piezoelectrically active material, such as a piezoelectric ceramic, crystal, plastic, and/or composite material, as well as lithium niobate, lead titanate, barium titanate, and/or lead metaniobate. In addition to, or instead of a piezoelectrically active material, transducer 19 can comprise any other materials configured for generating radiation and/or acoustical energy. Transducer 19 can also comprise one or more matching and/or backing layers configured along with the transduction elements such as coupled to the piezoelectrically active material. Transducer 19 can also be configured with single or multiple damping elements along the transduction elements.

In accordance with an exemplary embodiment, the thickness of the transduction elements of transducer 19 can be configured to be uniform. That is, the transduction elements can be configured to have a thickness that is substantially the same throughout. In accordance with another exemplary embodiment, the transduction elements can also be configured with a variable thickness, and/or as a multiple damped device. For example, the transduction elements of transducer 19 can be configured to have a first thickness selected to provide a center operating frequency of a lower range, for example from approximately 1 kHz to 3 MHz. Transduction element 26 can be configured with a second thickness selected to provide a center operating frequency of a higher range, for example from approximately 3 to 100 MHz, or more.

Transducer 19 can be configured as a single broadband transducer excited with at least two or more frequencies to provide an adequate output for raising the temperature within ROI 12 to a desired level. Transducer 19 can also be configured as two or more individual transducers, wherein each transducer 19 comprises transduction elements, the thickness of which may be selected as above to provide a desired center operating frequency.

Moreover, in an exemplary embodiment, any variety of mechanical lenses or variable focus lenses, e.g. liquid-filled lenses, may also be used to additionally focus and or defocus the energy field. For example, with reference to exemplary embodiments depicted in FIGS. 4A and 4B, transducer 19 may also be configured with an electronic focusing array 24 in combination with one or more transduction elements to facilitate increased flexibility in treating ROI 12. Array 24 may be configured in a manner similar to transducer 19. That is, array 24 can be configured as an array of electronic apertures that may be operated by a variety of phases via variable electronic time delays, for example, $T_i \ldots T_j$. By the term "operated," the electronic apertures of array 24 may be manipulated, driven, used, and/or configured to produce and/or deliver energy in a manner corresponding to the phase variation caused by electronic time delays. For example, these phase variations can be used to deliver defocused beams, planar beams, and/or focused beams, each of which may be used in combination to achieve different physiological effects in ROI 12.

Transduction elements may be configured to be concave, convex, and/or planar. For example, in an exemplary embodiment depicted in FIG. 4A, transduction elements 26A and 26B are configured to be concave in order to provide focused energy for treatment of ROI 12. Additional embodiments are disclosed in U.S. patent application Ser. No. 10/944,500, entitled "System and Method for Variable Depth Ultrasound Treatment", incorporated herein by reference. In an exemplary embodiment of FIG. 4A transduction elements 24 and associated time or phase delays are perpendicular to that shown in FIG. 4A, whereby such perpendicularly disposed transduction elements 24 are therapy, imaging, or dual-mode imaging-therapy elements.

In another exemplary embodiment, depicted in FIG. 4B, transduction elements 26A and 26B can be configured to be substantially flat in order to provide substantially uniform energy to ROI 12. In an exemplary embodiment of FIG. 4B transduction elements 24 and associated time or phase delays are perpendicular to that shown in FIG. 4B, whereby such perpendicularly disposed transduction elements 24 are therapy, imaging, or dual-mode imaging-therapy elements. While FIGS. 4A and 4B depict exemplary embodiments with the transduction elements configured as concave and substantially flat, respectively, the transduction elements can be configured to be concave, convex, and/or substantially flat. In addition, the transduction elements can be configured to be any combination of concave, convex, and/or substantially flat structures. For example, a first transduction element can be configured to be concave, while a second transduction element within transducer 19 can be configured to be substantially flat.

Figure 4C:
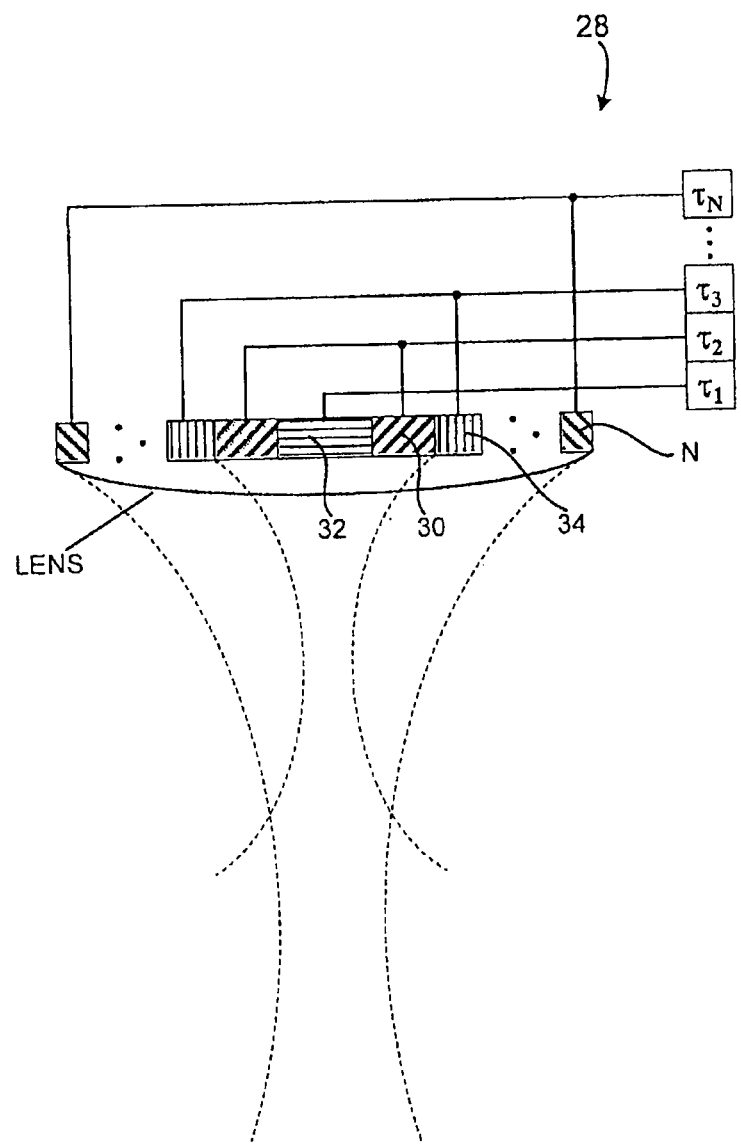
Figure 4D:
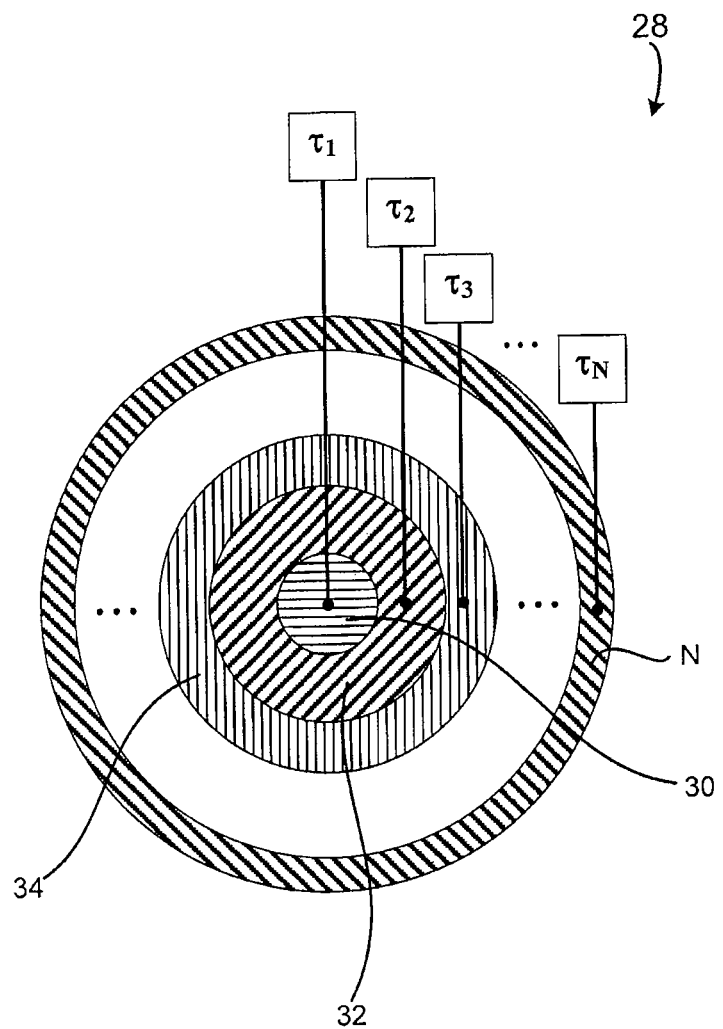

With reference to FIGS. 4C and 4D, transducer 19 can also be configured as an annular array to provide planar, focused and/or non-focused acoustical energy. For example, in accordance with an exemplary embodiment, an annular array 28 can comprise a plurality of rings 30, 32, 34 to N. Rings 30, 32, 34 to N can be mechanically and electrically isolated into a set of individual elements, and can create planar, focused, or non-focused waves. For example, such waves can be centered on-axis, such as by methods of adjusting corresponding transmit and/or receive delays, $T_1, T_2, T_3 \ldots TN$. An electronic focus can be suitably moved along various depth positions, and can enable variable strength or beam tightness, while an electronic defocus can have varying amounts of defocusing. In accordance with an exemplary embodiment, a lens and/or concave, convex, and/or substantially flat shaped annular array 28 can also be provided to aid focusing or defocusing such that any time differential delays can be reduced. Movement of annular array 28 in one, two or three-dimensions, or along any path, such as through use of probes and/or any conventional robotic arm mechanisms, may be implemented to scan and/or treat a volume or any corresponding space within ROI 12.

Figure 4E:
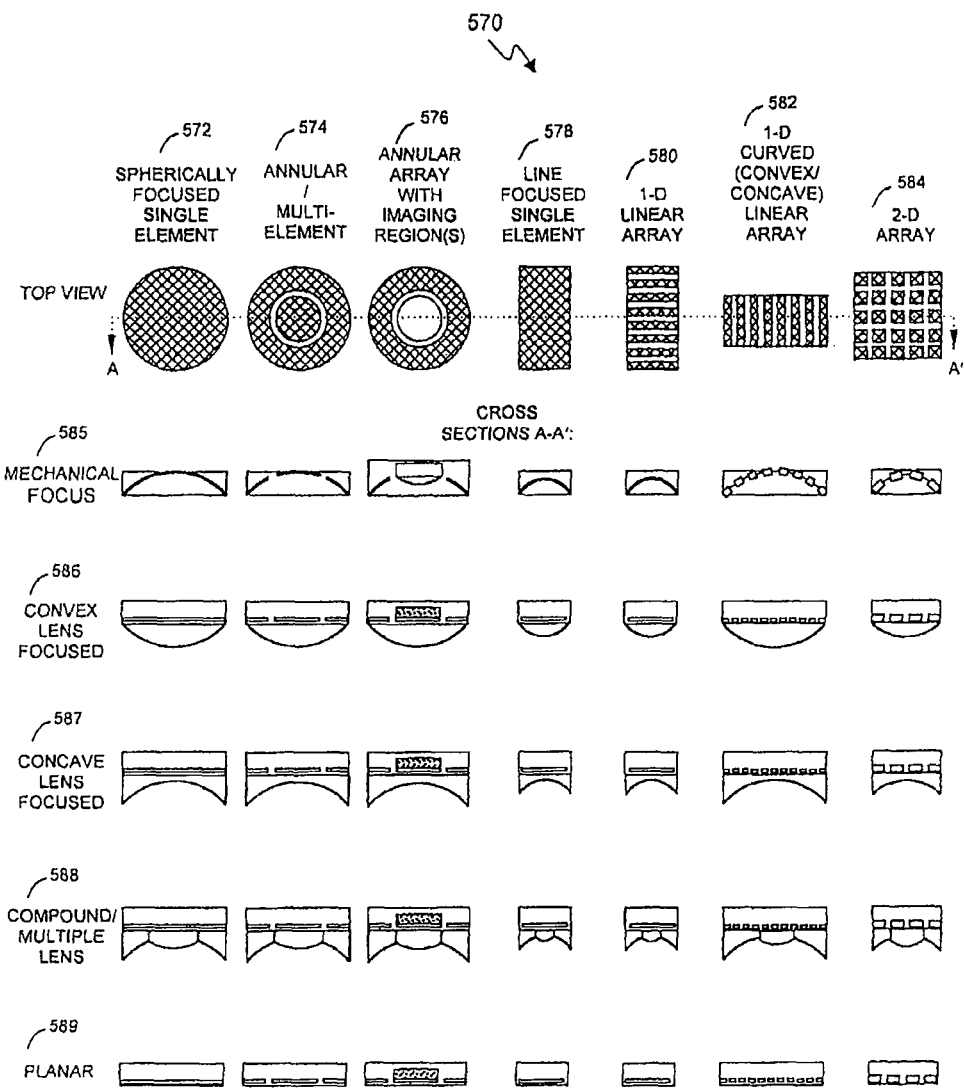

With reference to FIG. 4E, an exemplary transducer 570 can also be configured as a spherically focused single element 572, annular/multi-element 574, annular array with imaging region(s) 576, line focused single element 578, 1-D linear array 580, 1-D curved (convex/concave) linear array 582, and/or 2-D array 584, with mechanical focus 585, convex lens focus 586, concave lens focus 587, compound/multiple lens focus 588, and/or planar array form 589, to achieve focused, unfocused, or non-focused sound fields for both imaging and/or therapy. Other lens shapes can still be used in other exemplary embodiments of the present invention. Analogous to spherically focused single element 572 to be configured for multiple annulii 574 and/or imaging regions 576, an exemplary embodiment for the therapeutic line-focused single element 578, and 1-D and 2-D arrays 580, 582 and 584 is to dispose one or more imaging elements or imaging arrays in their aperture, such as along the center of their aperture. In general a combination of imaging and therapy transducers or dual mode imaging-therapy transducers can be utilized.

Figure 5A:
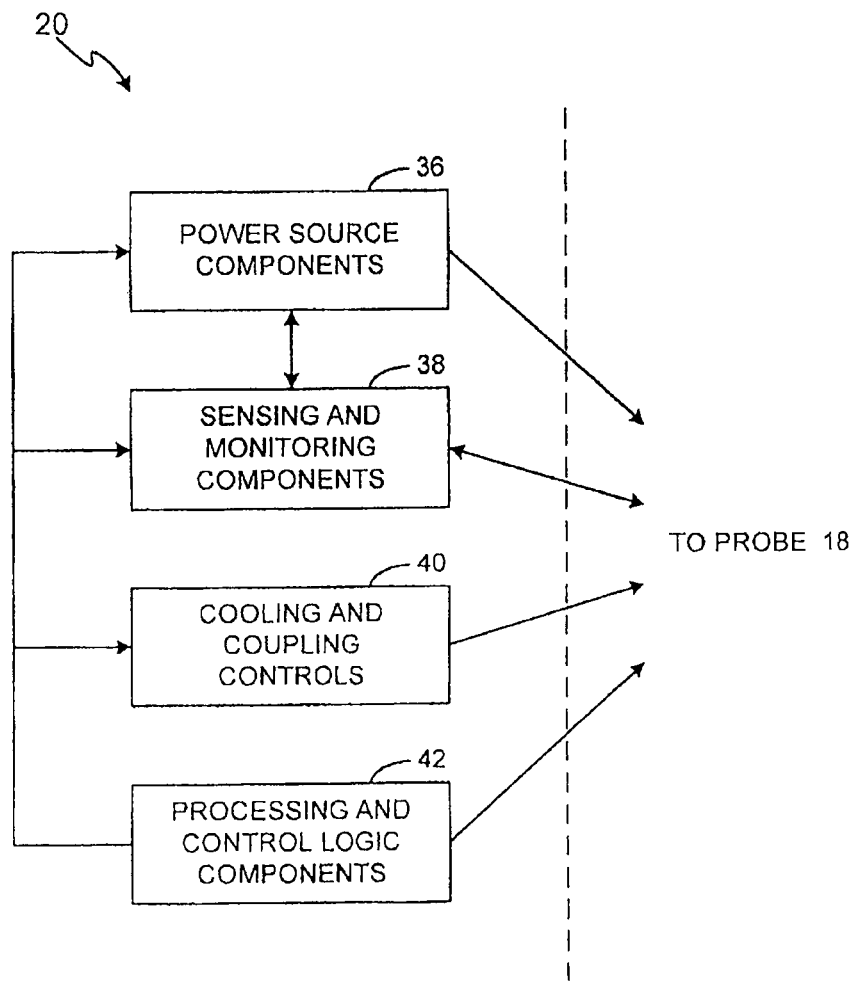
FIGS. 5A, 5B, and 5C illustrate block diagrams of an exemplary control system in accordance with exemplary embodiments of the present invention.
Figure 5B:
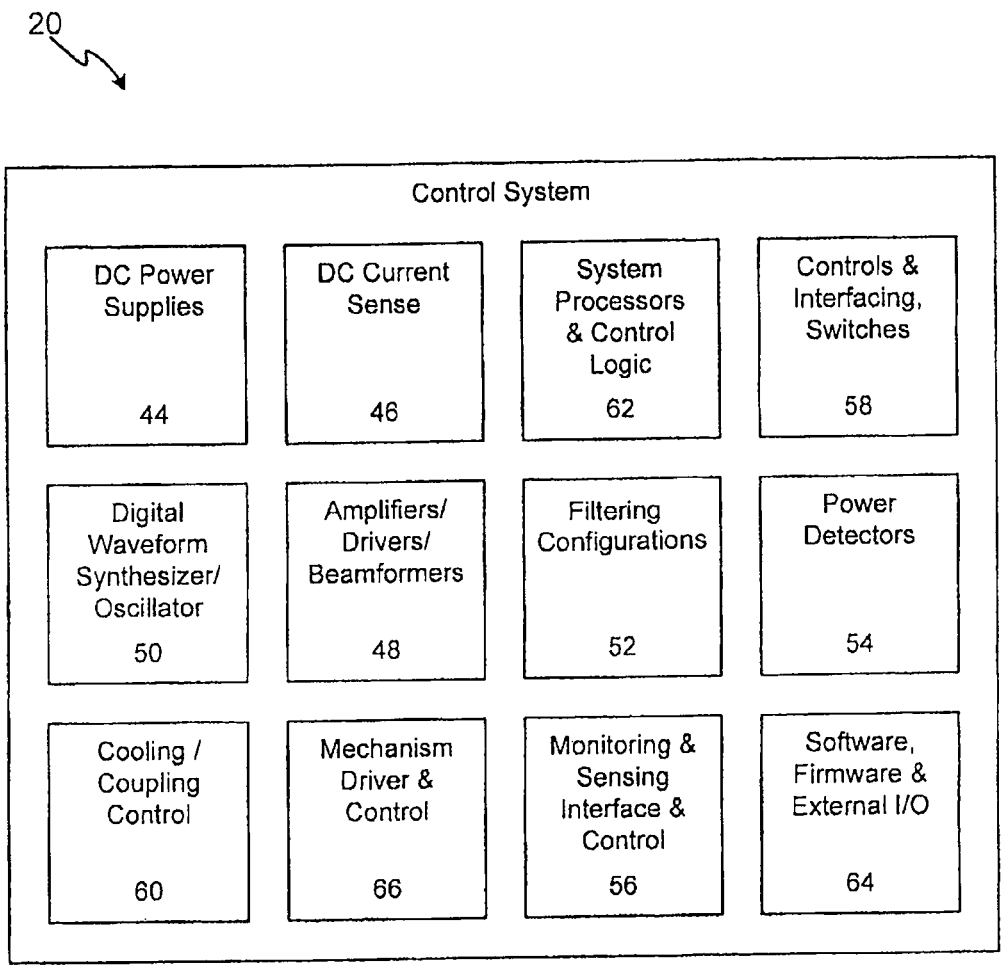

An exemplary transducer is suitably controlled and operated in various manners by control system 20. In an exemplary embodiment depicted in FIGS. 5A-5C, control system 20 is configured for coordination and control of the entire acoustic energy system. For example, control system 20 can suitably comprise power source components 36, sensing and monitoring components 38, cooling and coupling controls 40, and/or processing and control logic components 42. Control system 20 can be configured and optimized in a variety of ways with more or less subsystems and components to enhance therapy, imaging and/or monitoring, and the embodiments in FIGS. 5A and 5B are merely for illustration purposes.

For example, for power sourcing components 36, control system 20 can comprise one or more direct current (DC) power supplies 44 configured to provide electrical energy for entire control system 20, including power required by a transducer electronic amplifier/driver 48. A DC current sense device 46 can also be provided to confirm the level of power going into amplifiers/drivers 48 for safety and monitoring purposes.

Amplifiers/drivers 48 can comprise multi-channel or single channel power amplifiers and/or drivers. In accordance with an exemplary embodiment for transducer array configurations, amplifiers/drivers 48 can also be configured with a beamformer to facilitate array focusing. An exemplary beamformer can be electrically excited by a digitally controlled waveform synthesizer/oscillator 50 with related switching logic.

Power sourcing components 36 can also include various filtering configurations 52. For example, switchable harmonic filters and/or matching may be used at the output of amplifier/driver/beamformer 48 to increase the drive efficiency and effectiveness. Power detection components 54 may also be included to confirm appropriate operation and calibration. For example, electric power and other power detection components 54 may be used to monitor the amount of power going to probe 18.

Various sensing and monitoring components 38 may also be suitably implemented within control system 20. For example, in accordance with an exemplary embodiment, monitoring, sensing, interface and control components 56 may be configured to operate with various motion detection systems implemented within transducer 19 to receive and process information such as acoustic or other spatial and/or temporal information from ROI 12. Sensing and monitoring components 38 can also include various controls, interfacing and switches 58 and/or power detectors 54. Such sensing and monitoring components 38 can facilitate open-loop and/or closed-loop feedback systems within treatment system 14.

In an exemplary embodiment, sensing and monitoring components 38 comprise a sensor that is connected to an audio or visual alarm system to prevent overuse of system 14. In this exemplary embodiment, the sensor senses the amount of energy transferred to stratum corneum 85, viable epidermis 86, viable dermis 88, subcutaneous connective tissue and fat 82, or muscle 84, or the time that system 14 has be actively emitting energy. When a certain time or temperature threshold has been reached, the alarm sounds an audible alarm or causes a visual indicator to activate to alert the user that the threshold is reached. This prevents the user from overusing system 14. In an exemplary embodiment, the sensor could be operatively connected to control system 20 and force control system 20 to stop emitting ultrasound energy 2 and/or 4 from probe 18.

A cooling/coupling control system 60 may be provided to remove waste heat from an exemplary probe 18, provide a controlled temperature at the superficial tissue interface and deeper into tissue, and/or provide acoustic coupling from probe 18 to ROI 12. Such cooling/coupling control system 60 can also be configured to operate in both open-loop and/or closed-loop feedback arrangements with various coupling and feedback components.

Additionally, an exemplary control system 20 can further comprise various system processors and digital control logic 62, such as one or more controls or interfacing switches 58 and associated components, including firmware and software 64, which interfaces to user controls and interfacing circuits as well as input/output circuits and systems for communications, displays, interfacing, storage, documentation, and other useful functions. Software 64 controls all initialization, timing, level setting, monitoring, safety monitoring, and all other system functions required to accomplish user-defined treatment objectives. Further, various mechanisms 66 can also be suitably configured to control operation.

Figure 5C:
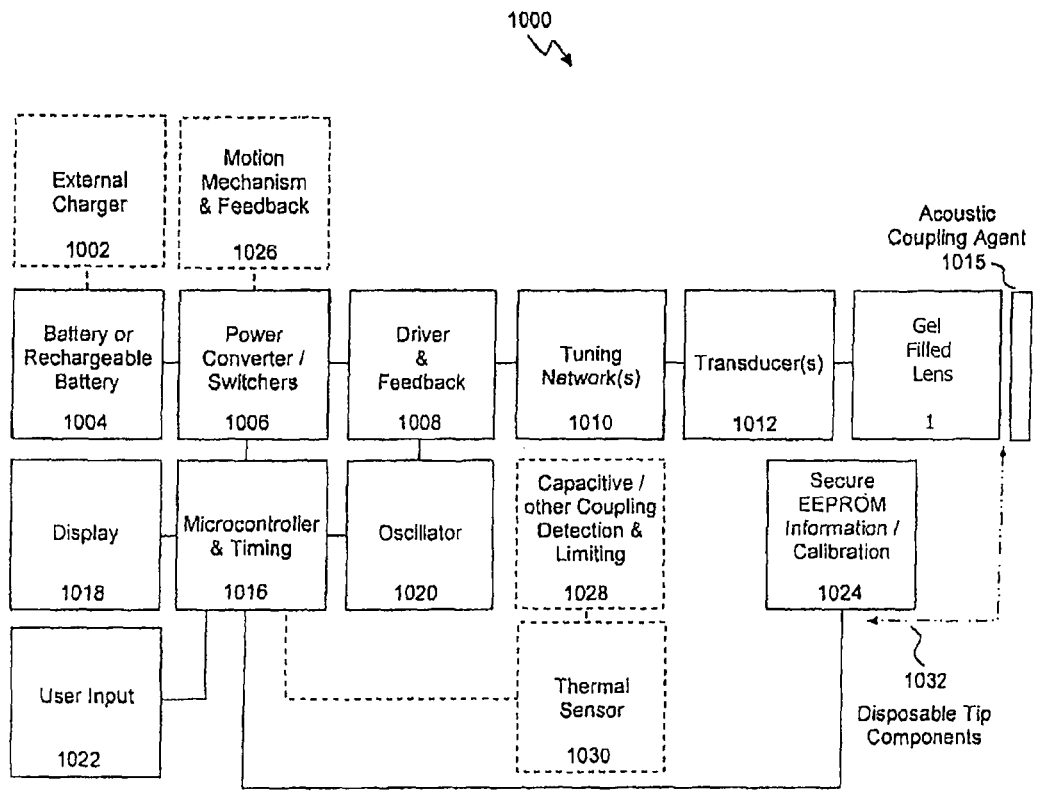

With reference to FIG. 5C, an exemplary transducer is suitably controlled and operated in various manners by a hand-held format control system 1000. An external battery charger 1002 can be used with rechargeable-type batteries 1004 or batteries 1004 can be single-use disposable types, such as AA-sized cells. Power converters 1006 produce voltages suitable for powering a driver/feedback circuit 1008 with tuning network 1010 driving a transducer 1012 coupled to the patient via one or more coupler members 1. In some embodiments, coupler member 1 is coupled to the patient with an acoustic coupling agent 1015. In addition, a microcontroller and timing circuits 1016 with associated software and algorithms provide control and user interfacing via a display 1018, oscillator 1020, and other input/output controls 1022 such as switches and audio devices. A storage element 1024, such as an EEPROM, secure EEPROM, tamper-proof EEPROM, or similar device holds calibration and usage data. A motion mechanism with feedback 1026 can be suitably controlled to scan the transducer, if desirable, in a line or two-dimensional pattern and/or with variable depth. Other feedback controls include a capacitive, acoustic, or other coupling detection means and/or limiting controls 1028 and thermal sensor 1030. A combination of the secure EEPROM with at least one of coupler members 1, transducer 1012, thermal sensor 1030, coupling detectors 1028, or tuning network 1010 along with a plastic or other housing can comprise a disposable tip 1032.

Figure 6:
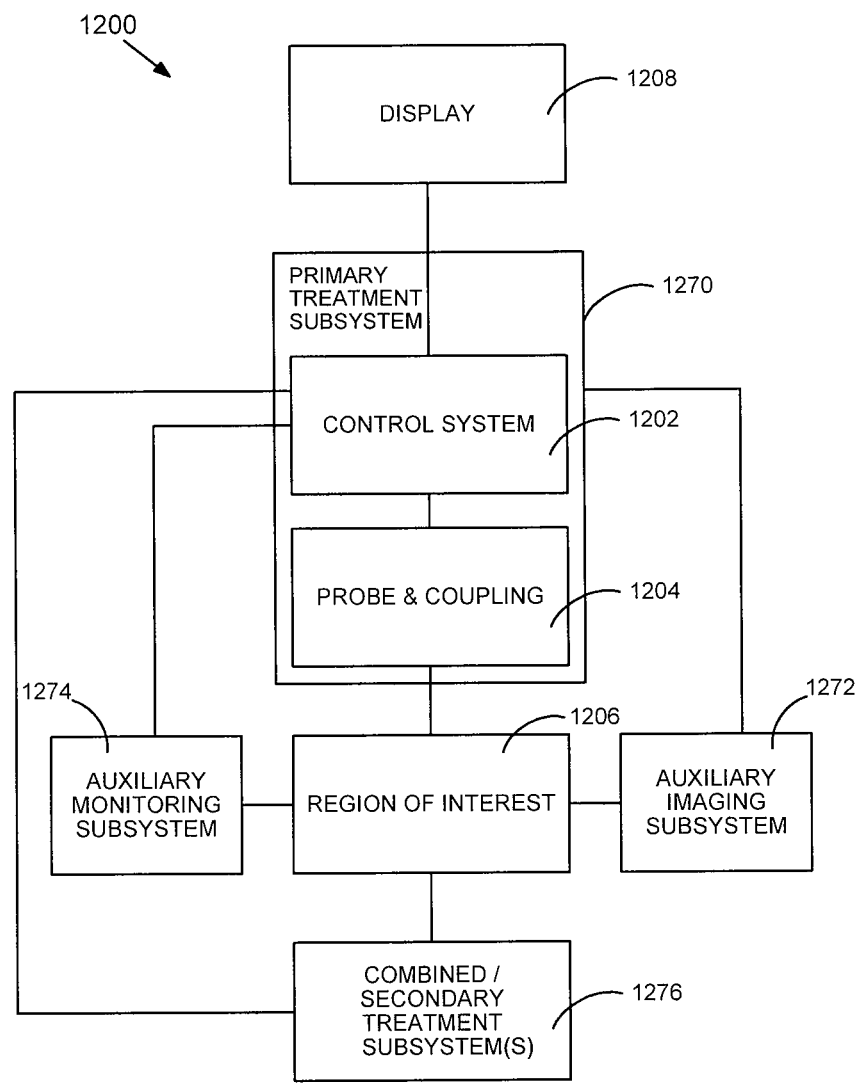
FIG. 6 illustrates a block diagram of a treatment system comprising an ultrasound treatment subsystem combined with additional subsystems and methods of treatment monitoring and/or treatment imaging as well as a secondary treatment subsystem in accordance with an exemplary embodiment of the present invention.

In accordance with another exemplary embodiment, with reference to FIG. 6, an exemplary treatment system 1200 can be configured with and/or combined with various auxiliary systems to provide additional functions. For example, an exemplary treatment system 1200 for treating a region of interest 1206 can comprise a control system 1202, a probe 1204, and a display 1208. Treatment system 1200 further comprises one or more of an auxiliary imaging modality 1274 and/or one or more of an auxiliary monitoring or sensing modality 1272, which may be based upon at least one of photography and other visual optical methods, magnetic resonance imaging (MRI), computed tomography (CT), optical coherence tomography (OCT), electromagnetic, microwave, or radio frequency (RF) methods, positron emission tomography (PET), infrared, ultrasound, acoustic, or any other suitable method of visualization, localization, or monitoring within region-of-interest 1206, including imaging/monitoring enhancements. Such imaging/monitoring enhancement for ultrasound imaging via probe 1204 and control system 1202 could comprise M-mode, persistence, filtering, color, Doppler, and harmonic imaging among others; furthermore an ultrasound treatment system 1270, as a primary source of treatment, may be combined with a secondary source of treatment 1276, including radio frequency (RF) energy, microwave energy, or other photon based energy methods including intense pulsed light (IPL), laser, infrared laser, microwave, or any other suitable energy source. A multi-modality coupler analogous to FIG. 1B is a particularly useful embodiment for a multi-modality treatment, sensing, monitoring and imaging system.

With reference again to FIG. 3, an exemplary system 14 also includes display system 22 to provide images of the ROI 12 in certain exemplary embodiments wherein ultrasound energy is emitted from transducer 19 in a manner suitable for imaging. Display system can be any type of system that conveys images or information apart from images about system 14 or ROI 12 to the user. Therefore, display system 22 can be a computer monitor, television screen or it can be a simply type of indicator system such a liquid crystal display or light emitting diode display in various exemplary embodiments. Liquid crystal displays and light emitting diode displays are particularly useful when system 14 is a hand-held system.

Display system 22 enables the user to facilitate localization of the treatment area and surrounding structures, e.g., identification of cell membranes or tissues. After localization, delivery of ultrasound energy 2 and/or 4 at a depth, distribution, timing, and energy level is provided, to achieve the desired therapy, imaging and/or monitoring. Before, during, and/or after therapy, i.e., before, during and/or after delivery of ultrasound energy, monitoring of the treatment area and surrounding structures can be conducted to further plan and assess the results and/or provide feedback to control system 20 and a system operator via display system 22. In accordance with an exemplary embodiment, localization can be facilitated through ultrasound imaging that can be used to define an ROI 12 within one or more layers of skin tissue.

For ultrasound energy delivery, transducer 19 can be mechanically and/or electronically scanned to place treatment zones over an extended area in ROI 12. A treatment depth can be adjusted between a range of approximately 1 to 100 millimeters, and/or the greatest depth of muscle 84. Such delivery of energy can occur through imaging of the targeted cell membrane or tissue and then applying ultrasound energy, or application of ultrasound energy at known depths over an extended area without initial or ongoing imaging.

The ultrasound beam from transducer 19 can be spatially and/or temporally controlled by changing the spatial parameters of transducer 19, such as the placement, distance, treatment depth and transducer 19 structure, as well as by changing the temporal parameters of transducer 19, such as the frequency, drive amplitude, and timing, with such control handled via control system 20. Such spatial and temporal parameters can also be suitably monitored and/or utilized in open-loop and/or closed-loop feedback systems within ultrasound system 16.

In accordance with another exemplary embodiment of the present invention, with reference again to FIG. 3, an exemplary monitoring method may comprise monitoring the temperature profile or other tissue parameters of ROI 12, such as attenuation, speed of sound, or mechanical properties such as stiffness and strain of the treatment region and suitably adjust the spatial and/or temporal characteristics and energy levels of ultrasound energy 2 and/or 4 emitted from transducer 19. The results of such monitoring techniques may be indicated on display system 22 by means of one-, two-, or three-dimensional images of monitoring results, or may simply comprise a success or fail-type indicator, or combinations thereof. Additional treatment monitoring techniques may be based on one or more of temperature, video, profilometry, and/or stiffness or strain gauges or any other suitable sensing technique.

Any amount of energy can be used as long as the tissue within ROI 12 is not ablated or coagulated. In an exemplary embodiment, the energy emitted from probe 18 is unfocused or defocused ultrasound energy 2 and/or 4. Alternatively, focused ultrasound energy 2 and/or 4 could be emitted from probe 18 and applied to ROI 12.

In one exemplary embodiment, the energy released into ROI 12 increases the local temperature within ROI 12 from approximately 1°-25° C. over a body's normal temperature. Therefore the temperature within ROI 12 during treatment is between approximately 35°-60° C. In another exemplary embodiment, the temperature is raised approximately 1°-15° C. over a body's normal temperature. Therefore, in this embodiment, the temperature within ROI 12 is between approximately 35°-49° C. While specific temperature ranges are disclosed herein, it should be noted that any temperature is considered to fall within the scope of the present invention.

In certain embodiments, the temperature increase may be very high but applied for a short enough time period so that the energy delivered to ROI 12 does not cause tissue ablation or coagulation. In other situations, the temperature increase may be fairly small and applied long enough to have an effect without causing tissue ablation or coagulation.

The time-temperature profile can be modeled and optimized with the aid of the thermal dose concept. The thermal dose, or $t_{43}$, is the exposure time at 43° C. which causes an equivalent biological effect due to an arbitrary time-temperature heating profile. Typically an ablative lesion forms on the order of one second at 56° C., which corresponds to a thermal dose of one hundred and twenty minutes at 43° C. The same thermal dose corresponds to 50° C. for approximately one minute. Thus a non-ablative profile can contain high temperatures for very short times and/or lower temperatures for longer times or a combination of various time-temperature profiles. For example, temperatures as high as 56° C. for under one second or 46° C. for under fifteen minutes can be utilized. Such processes can be implemented in various exemplary embodiments, whereby one or more profiles may be combined into a single treatment.

In an exemplary embodiment the temperature at ROI 12 is raised to a high level, such as approximately 50° C. or more and held for several seconds. In another exemplary embodiment, the temperature is raised to a high level, (for example greater than 50° C.), for under one second up to five seconds or more, and then turned off for under one second up to five seconds or more, and repeated to create a pulsed profile.

In another exemplary embodiment, the temperature is raised quickly to a high level (greater than 50° C.), and then dropped to a lower temperature (less than 50° C.), and then maintained at that temperature for a given time period such as one second up to several seconds or over a minute.

In another exemplary embodiment, the temperature is increased quickly to a high level ($T_{HIGH}$), whereby $T_{HIGH}$ is greater than 40° C., and the power to system 14 is turned off, but turned on again once the temperature drops below a lower threshold, ($T_{LOW}$), whereby $T_{LOW}$ is less than $T_{HIGH}$. Once the temperature reaches $T_{HIGH}$ again power to system 14 is turned back off and this process is repeated, in effect acting like a thermostat. The process is terminated after a total treatment time of under one second to one minute or more.

In another exemplary embodiment, the temperature is raised quickly to a high level ($T_{START}$), whereby $T_{START}$ is greater than 40° C. and then turned off, but turned on again before the temperature drops appreciably (i.e. by a few degrees) below $T_{START}$, whereby the temperature may then increase a small amount (i.e. by a few degrees) over $T_{START}$ before the power is turned off again. In such an exemplary embodiment the temperature quickly reaches a starting point and then may be allowed to increase to a higher temperature yet still remain in a non-ablative or coagulative regime before the treatment is ended.

The present invention may be described herein in terms of various functional components and processing steps. It should be appreciated that such components and steps may be realized by any number of hardware components configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of medical contexts and that the exemplary embodiments relating to a system as described herein are merely indicative of exemplary applications for the invention. For example, the principles, features and methods discussed may be applied to any medical application. Further, various aspects of the present invention may be suitably applied to other applications, such as other medical or industrial applications.

We claim:

1. A system for coupling acoustic energy to a region of interest comprising:
    a crystallized gel comprising water in an amount of from about 10% to about 90% mass, and polyvinyl alcohol in an amount of from about 2% to about 30% mass;
    a lens shaped into the crystallized gel;
    an ultrasound transducer integrated into the crystallized gel and positioned to emit ultrasound energy through the lens, wherein the crystallized gel is configured to at least one of raise and lower an attenuation of the ultrasound energy;
    at least one acoustic impedance matching layer positioned in a path of the ultrasound energy;
    an enclosure coupled to the crystallized gel;
    at least one of a power supply within the enclosure, the power supply coupled to the ultrasound transducer and configured to provide power to the ultrasound transducer to emit the ultrasound energy;
    a controller within the enclosure, and configured to control power and frequency of the ultrasound energy;
    a sensor in communication with the controller and configured to communicate a condition of the ultrasound energy; and
    an indicator displaying the condition of the ultrasound energy.

2. The system according to claim 1, wherein the crystallized gel further comprises a surfactant configured for the crystallized gel to be free of bubbles.

3. The system according to claim 1, wherein the crystallized gel is free of bubbles.

4. The system according to claim 1, wherein the crystallized gel is configured to alter at least one of an acoustic impedance and an acoustic velocity of the ultrasound energy.

5. The system according to claim 1, wherein the crystallized gel is configured for direct contact to a surface above a region of interest, and is configured to couple the ultrasound enemy emitted by the transducer to the region of interest.

6. A system for coupling acoustic energy to a region of interest comprising:
    a crystallized gel comprising water in an amount of from about 10% to about 90% mass, an and polyvinyl alcohol in an amount of from about 2% to about 30% mass;
    a lens shaped into the crystallized gel;
    an ultrasound transducer integrated into the crystallized gel and positioned to emit ultrasound energy through the lens wherein the crystallized gel is configured to alter at least one of an acoustic impedance and an acoustic velocity of the ultrasound energy;
    at least one acoustic impedance matching layer positioned in a path of the ultrasound energy;
    an enclosure coupled to the crystallized gel;
    at least one of a power supply within the enclosure, the power supply coupled to the ultrasound transducer and configured to provide power to the ultrasound transducer to emit the ultrasound energy;
    a controller within the enclosure; and configured to control power and frequency of the ultrasound energy;
    a sensor in communication with the controller and configured to communicate a condition of the ultrasound energy; and
    an indicator displaying the condition of the ultrasound energy.

7. The system according to claim 6, wherein the crystallized gel further comprises a surfactant configured for the crystallized gel to be free of bubbles.

8. The system according to claim 6, wherein the crystallized gel is configured to lower an attenuation of the ultrasound energy.

9. The system according to claim 6, wherein the crystallized gel is free of bubbles.

10. The system according to claim 6, wherein the crystallized gel is configured for direct contact to a surface above a region of interest, and is configured to couple the ultrasound energy emitted by the transducer to the region of interest.

11. A system for coupling acoustic energy to a region of interest comprising:
    a crystallized gel comprising water in an amount of from about 10% to about 90% mass, and polyvinyl alcohol in an amount of from about 2% to about 30% mass; and a lens shaped into the crystallized gel;
    an ultrasound transducer integrated into the crystallized gel and positioned to emit ultrasound energy through the lens;
    at least one acoustic impedance matching layer positioned in a path of the ultrasound energy;
    an enclosure coupled to the crystallized gel;
    at least one of a power supply within the enclosure, the power supply coupled to the ultrasound transducer and configured to provide power to the ultrasound transducer to emit the ultrasound energy;
    a controller within the enclosure, and configured to control power and frequency of the ultrasound energy;
    a sensor in communication with the controller and configured to communicate a condition of the ultrasound energy; and
    an indicator displaying the condition of the ultrasound energy;
    wherein the crystallized gel is configured for direct contact to a surface above a region of interest, and is configured to couple the ultrasound energy emitted by the transducer to the region of interest.

12. The system according to claim 11, wherein the crystallized gel further comprises a surfactant configured for the crystallized gel to be free of bubbles.

13. The system according to claim 11, wherein the crystallized gel is configured to lower an attenuation of the ultrasound energy.

14. The system according to claim 11, wherein the crystallized gel is free of bubbles.

15. The system according to claim 11, wherein the crystallized gel is configured to alter at least one of an acoustic impedance and an acoustic velocity of the ultrasound energy.

* * * * *